(12) United States Patent
Yang et al.

(10) Patent No.: US 9,040,298 B2
(45) Date of Patent: May 26, 2015

(54) METHOD OF SELECTING STEM CELLS HAVING HIGH CHONDROGENIC DIFFERENTIATION CAPABILITY

(75) Inventors: Yoon-Sun Yang, Seoul (KR); Won Il Oh, Seoul (KR); Hong Bae Jeon, Seoul (KR); Mee Hyun Jung, Seoul (KR); Sang Young Jeong, Seoul (KR)

(73) Assignee: Medipost Co., Ltd., Seoul (KR)

( * ) Notice: Subject to any disclaimer, the term of this patent is extended or adjusted under 35 U.S.C. 154(b) by 868 days.

(21) Appl. No.: 12/790,268

(22) Filed: May 28, 2010

(65) Prior Publication Data

US 2010/0303773 A1   Dec. 2, 2010

Related U.S. Application Data

(60) Provisional application No. 61/182,484, filed on May 29, 2009.

(30) Foreign Application Priority Data

May 13, 2010   (KR) .......................... 10-2010-0045128

(51) Int. Cl.
| | | |
|---|---|---|
| *C12N 5/00* | (2006.01) | |
| *A61K 38/17* | (2006.01) | |
| *A61K 38/18* | (2006.01) | |
| *A61K 38/39* | (2006.01) | |

(52) U.S. Cl.
CPC ......... *A61K 38/1709* (2013.01); *A61K 38/1808* (2013.01); *A61K 38/39* (2013.01)

(58) Field of Classification Search
None
See application file for complete search history.

(56) References Cited

U.S. PATENT DOCUMENTS

| | | | |
|---|---|---|---|
| 6,933,326 B1 * | 8/2005 | Griffey et al. ................. | 523/113 |
| 2008/0014179 A1 * | 1/2008 | Ferree ......................... | 424/93.7 |
| 2009/0232777 A1 * | 9/2009 | Lundgren-Akerlund et al. ........................... | 424/93.7 |
| 2010/0303773 A1 | 12/2010 | Yang et al. | |

FOREIGN PATENT DOCUMENTS

| | | |
|---|---|---|
| JP | 2008-289476 | 12/2008 |
| WO | WO-03070922 A1 | 8/2003 |
| WO | WO 2010/131917 A2 | 11/2010 |

OTHER PUBLICATIONS

International Search Report dated Apr. 28, 2011 in PCT International Application No. PCT/KR2010/003040, filed May 13; 2010.

Written Opinion dated Apr. 28, 2011 in PCT International Application No. PCT/KR2010/003040, filed May 13, 2010.
Bornstein et al., "Thrombospondin 2, a matricellular protein with diverse functions," Matrix Biology, vol. 19, pp. 557-568 (2000).
Sekiya et al., "In vitro cartilage formation by human adult stem cells from bone marrow stroma defines the sequence of cellular and molecular events during chondrogenesis," PNAS, vol. 99, No. 7, pp. 4397-4402 (2000).
Sekiya et al., "Expansion of Human Adult Stem Cells from Bone Marrow Stroma: Conditions that Maximize the Yields of Early Progenitors and Evaluate Their Quality," Stem Cells, vol. 20, pp. 530-541 (2002).
Indrawattana et al., "Growth factor combination for chondrogenic induction from human mesenchymal stem cell," Biochemical and Biophysical Research Communications, vol. 320, pp. 914-919 (2004).
Krampera et al., "HB-EGF/HER-1 signaling in bone marrow mesenchymal stem cells: inducing cell expansion and reversibly preventing multilineage differentiation," Blood, vol. 106, No. 1, pp. 59-66 (2005).
Hwang et al., "Morphogenetic Signals from Chondrocytes Promote Chondrogenic and Osteogenic Differentiation of Mesenchymal Stem Cells," Journal of Cellular Physiology, vol. 212, pp. 281-284 (2007).
Aung et al., "Osteoarthritic Chondrocyte-Secreted Morphogens Induce Chondrogenic Differentiation of Human Mesenchymal Stem Cells," Arthritis & Rheumatism, vol. 63, No. 1, pp. 148-158 (2011).
Korean Office Action dated Apr. 26, 2012, in Korean Patent Application No. 10-2010-0045128.
Zhang et al., "Microarray analysis of perichondral and reserve growth plate zones identifies differential gene expressions and signal pathways," Bone, vol. 43, 2008, pp. 511-520.
Taylor et al., "Thrombospondin-2 Influences the Proportion of Cartilage and Bone During Fracture Healing," Journal of Bone and Mineral Research, vol. 24, No. 6, 2009, pp. 1043-1054.
Kokubu et al., "Immunolocalization of IL-17A, IL-17B, and Their Receptors in Chondrocytes During Fracture Healing," Journal of Histochemistry & Cytochemistry, vol. 56, No. 2, 2008, pp. 89-95.
Mackay A M et al.,"Chondrogenic differentiation of cultured human mesenchymal stem cells from marrow," Tissue Eng. 1998 Winter 4(4):415-28.
Palmer G D et al., "Gene-induced chondrogenesis of primary mesenchymal stem cells in vitro," Mol Ther. Aug. 2005 12(2):219-28.
Supplementary European Search Report issued May 7, 2013 in European Application No. 10775119.0.
Japanese Office Action dated Sep. 2, 2014, in Japanese Patent Application No. 2012- 510753 (4 pages).

* cited by examiner

*Primary Examiner* — Blaine Lankford
(74) *Attorney, Agent, or Firm* — Drinker Biddle & Reath LLP

(57) ABSTRACT

Thrombospondin 1 (TSP-1), TSP-2, interleukin 17B receptor (IL-17BR) and heparin-binding epidermal growth factor-like growth factor (HB-EGF) associated with stem cell activity and use thereof.

5 Claims, 23 Drawing Sheets
(6 of 23 Drawing Sheet(s) Filed in Color)

| | -SNP | +SNP (500μM) | +SNP (750μM) |
|---|---|---|---|
| CHONDROCYTE | | | |
| CHONDROCYTE (with HB-EGF : 50ng/ml) | | | |

SEQUENCE LISTING

```
<160> NUMBER OF SEQ ID NOS: 10

<210> SEQ ID NO 1
<211> LENGTH: 1172
<212> TYPE: PRT
<213> ORGANISM: Homo sapiens

<400> SEQUENCE: 1

Met Val Trp Arg Leu Val Leu Leu Ala Leu Trp Val Trp Pro Ser Thr
  1               5                  10                  15

Gln Ala Gly His Gln Asp Lys Asp Thr Thr Phe Asp Leu Phe Ser Ile
                 20                  25                  30

Ser Asn Ile Asn Arg Lys Thr Ile Gly Ala Lys Gln Phe Arg Gly Pro
             35                  40                  45

Asp Pro Gly Val Pro Ala Tyr Arg Phe Val Arg Phe Asp Tyr Ile Pro
         50                  55                  60

Pro Val Asn Ala Asp Asp Leu Ser Lys Ile Thr Lys Ile Met Arg Gln
 65                  70                  75                  80

Lys Glu Gly Phe Phe Leu Thr Ala Gln Leu Lys Gln Asp Gly Lys Ser
                 85                  90                  95

Arg Gly Thr Leu Leu Ala Leu Glu Gly Pro Gly Leu Ser Gln Arg Gln
            100                 105                 110

Phe Glu Ile Val Ser Asn Gly Pro Ala Asp Thr Leu Asp Leu Thr Tyr
        115                 120                 125

Trp Ile Asp Gly Thr Arg His Val Val Ser Leu Glu Asp Val Gly Leu
    130                 135                 140

Ala Asp Ser Gln Trp Lys Asn Val Thr Val Gln Val Ala Gly Glu Thr
145                 150                 155                 160
```

-continued

```
Tyr Ser Leu His Val Gly Cys Asp Leu Ile Asp Ser Phe Ala Leu Asp
            165                 170                 175
Glu Pro Phe Tyr Glu His Leu Gln Ala Glu Lys Ser Arg Met Tyr Val
        180                 185                 190
Ala Lys Gly Ser Ala Arg Glu Ser His Phe Arg Gly Leu Leu Gln Asn
    195                 200                 205
Val His Leu Val Phe Glu Asn Ser Val Glu Asp Ile Leu Ser Lys Lys
210                 215                 220
Gly Cys Gln Gln Gly Gln Gly Ala Glu Ile Asn Ala Ile Ser Glu Asn
225                 230                 235                 240
Thr Glu Thr Leu Arg Leu Gly Pro His Val Thr Thr Glu Tyr Val Gly
                245                 250                 255
Pro Ser Ser Glu Arg Arg Pro Glu Val Cys Glu Arg Ser Cys Glu Glu
            260                 265                 270
Leu Gly Asn Met Val Gln Glu Leu Ser Gly Leu His Val Leu Val Asn
        275                 280                 285
Gln Leu Ser Glu Asn Leu Lys Arg Val Ser Asn Asp Asn Gln Phe Leu
    290                 295                 300
Trp Glu Leu Ile Gly Gly Pro Pro Lys Thr Arg Asn Met Ser Ala Cys
305                 310                 315                 320
Trp Gln Asp Gly Arg Phe Phe Ala Glu Asn Glu Thr Trp Val Val Asp
                325                 330                 335
Ser Cys Thr Thr Cys Thr Cys Lys Lys Phe Lys Thr Ile Cys His Gln
            340                 345                 350
Ile Thr Cys Pro Pro Ala Thr Cys Ala Ser Pro Ser Phe Val Glu Gly
        355                 360                 365
Glu Cys Cys Pro Ser Cys Leu His Ser Val Asp Gly Glu Glu Gly Trp
    370                 375                 380
Ser Pro Trp Ala Glu Trp Thr Gln Cys Ser Val Thr Cys Gly Ser Gly
385                 390                 395                 400
Thr Gln Gln Arg Gly Arg Ser Cys Asp Val Thr Ser Asn Thr Cys Leu
                405                 410                 415
Gly Pro Ser Ile Gln Thr Arg Ala Cys Ser Leu Ser Lys Cys Asp Thr
            420                 425                 430
Arg Ile Arg Gln Asp Gly Gly Trp Ser His Trp Ser Pro Trp Ser Ser
        435                 440                 445
Cys Ser Val Thr Cys Gly Val Gly Asn Ile Thr Arg Ile Arg Leu Cys
    450                 455                 460
Asn Ser Pro Val Pro Gln Met Gly Gly Lys Asn Cys Lys Gly Ser Gly
465                 470                 475                 480
Arg Glu Thr Lys Ala Cys Gln Gly Ala Pro Cys Pro Ile Asp Gly Arg
                485                 490                 495
Trp Ser Pro Trp Ser Pro Trp Ser Ala Cys Thr Val Thr Cys Ala Gly
            500                 505                 510
Gly Ile Arg Glu Arg Thr Arg Val Cys Asn Ser Pro Glu Pro Gln Tyr
        515                 520                 525
Gly Gly Lys Ala Cys Val Gly Asp Val Gln Glu Arg Gln Met Cys Asn
    530                 535                 540
Lys Arg Ser Cys Pro Val Asp Gly Cys Leu Ser Asn Pro Cys Phe Pro
545                 550                 555                 560
Gly Ala Gln Cys Ser Ser Phe Pro Asp Gly Ser Trp Ser Cys Gly Ser
                565                 570                 575
```

```
Cys Pro Val Gly Phe Leu Gly Asn Gly Thr His Cys Glu Asp Leu Asp
            580                 585                 590

Glu Cys Ala Leu Val Pro Asp Ile Cys Phe Ser Thr Ser Lys Val Pro
        595                 600                 605

Arg Cys Val Asn Thr Gln Pro Gly Phe His Cys Leu Pro Cys Pro Pro
    610                 615                 620

Arg Tyr Arg Gly Asn Gln Pro Val Gly Val Gly Leu Glu Ala Ala Lys
625                 630                 635                 640

Thr Glu Lys Gln Val Cys Glu Pro Glu Asn Pro Cys Lys Asp Lys Thr
                645                 650                 655

His Asn Cys His Lys His Ala Glu Cys Ile Tyr Leu Gly His Phe Ser
            660                 665                 670

Asp Pro Met Tyr Lys Cys Glu Cys Gln Thr Gly Tyr Ala Gly Asp Gly
        675                 680                 685

Leu Ile Cys Gly Glu Asp Ser Asp Leu Asp Gly Trp Pro Asn Leu Asn
    690                 695                 700

Leu Val Cys Ala Thr Asn Ala Thr Tyr His Cys Ile Lys Asp Asn Cys
705                 710                 715                 720

Pro His Leu Pro Asn Ser Gly Gln Glu Asp Phe Asp Lys Asp Gly Ile
                725                 730                 735

Gly Asp Ala Cys Asp Asp Asp Asp Asn Asp Gly Val Thr Asp Glu
            740                 745                 750

Lys Asp Asn Cys Gln Leu Leu Phe Asn Pro Arg Gln Ala Asp Tyr Asp
        755                 760                 765

Lys Asp Glu Val Gly Asp Arg Cys Asp Asn Cys Pro Tyr Val His Asn
770                 775                 780

Pro Ala Gln Ile Asp Thr Asp Asn Asn Gly Glu Gly Asp Ala Cys Ser
785                 790                 795                 800

Val Asp Ile Asp Gly Asp Asp Val Phe Asn Glu Arg Asp Asn Cys Pro
                805                 810                 815

Tyr Val Tyr Asn Thr Asp Gln Arg Asp Thr Asp Gly Asp Gly Val Gly
            820                 825                 830

Asp His Cys Asp Asn Cys Pro Leu Val His Asn Pro Asp Gln Thr Asp
        835                 840                 845

Val Asp Asn Asp Leu Val Gly Asp Gln Cys Asp Asn Asn Glu Asp Ile
850                 855                 860

Asp Asp Asp Gly His Gln Asn Asn Gln Asp Asn Cys Pro Tyr Ile Ser
865                 870                 875                 880

Asn Ala Asn Gln Ala Asp His Asp Arg Asp Gly Gln Gly Asp Ala Cys
                885                 890                 895

Asp Pro Asp Asp Asp Asn Asp Gly Val Pro Asp Asp Arg Asp Asn Cys
            900                 905                 910

Arg Leu Val Phe Asn Pro Asp Gln Glu Asp Leu Asp Gly Asp Gly Arg
        915                 920                 925

Gly Asp Ile Cys Lys Asp Asp Phe Asp Asn Asp Asn Ile Pro Asp Ile
    930                 935                 940

Asp Asp Val Cys Pro Glu Asn Asn Ala Ile Ser Glu Thr Asp Phe Arg
945                 950                 955                 960

Asn Phe Gln Met Val Pro Leu Asp Pro Lys Gly Thr Thr Gln Ile Asp
                965                 970                 975

Pro Asn Trp Val Ile Arg His Gln Gly Lys Glu Leu Val Gln Thr Ala
            980                 985                 990
```

-continued

```
Asn Ser Asp Pro Gly Ile Ala Val Gly Phe Asp Glu Phe Gly Ser Val
        995                 1000                1005

Asp Phe Ser Gly Thr Phe Tyr Val Asn Thr Asp Arg Asp Asp Asp Tyr
        1010                1015                1020

Ala Gly Phe Val Phe Gly Tyr Gln Ser Ser Arg Phe Tyr Val Val
1025                1030                1035                1040

Met Trp Lys Gln Val Thr Gln Thr Tyr Trp Glu Asp Gln Pro Thr Arg
        1045                1050                1055

Ala Tyr Gly Tyr Ser Gly Val Ser Leu Lys Val Val Asn Ser Thr Thr
        1060                1065                1070

Gly Thr Gly Glu His Leu Arg Asn Ala Leu Trp His Thr Gly Asn Thr
        1075                1080                1085

Pro Gly Gln Val Arg Thr Leu Trp His Asp Pro Arg Asn Ile Gly Trp
        1090                1095                1100

Lys Asp Tyr Thr Ala Tyr Arg Trp His Leu Thr His Arg Pro Lys Thr
1105                1110                1115                1120

Gly Tyr Ile Arg Val Leu Val His Glu Gly Lys Gln Val Met Ala Asp
                1125                1130                1135

Ser Gly Pro Ile Tyr Asp Gln Thr Tyr Ala Gly Gly Arg Leu Gly Leu
        1140                1145                1150

Phe Val Phe Ser Gln Glu Met Val Tyr Phe Ser Asp Leu Lys Tyr Glu
        1155                1160                1165

Cys Arg Asp Ile
        1170

<210> SEQ ID NO 2
<211> LENGTH: 1172
<212> TYPE: PRT
<213> ORGANISM: Mus musculus

<400> SEQUENCE: 2

Met Leu Trp Ala Leu Ala Leu Leu Ala Leu Gly Ile Gly Pro Arg Ala
1               5                   10                  15

Ser Ala Gly Asp His Val Lys Asp Thr Ser Phe Asp Leu Phe Ser Ile
                20                  25                  30

Ser Asn Ile Asn Arg Lys Thr Ile Gly Ala Lys Gln Phe Arg Gly Pro
            35                  40                  45

Asp Pro Gly Val Pro Ala Tyr Arg Phe Val Arg Phe Asp Tyr Ile Pro
        50                  55                  60

Pro Val Asn Thr Asp Asp Leu Asn Arg Ile Val Lys Leu Ala Arg Arg
65                  70                  75                  80

Lys Glu Gly Phe Phe Leu Thr Ala Gln Leu Lys Gln Asp Arg Lys Ser
                85                  90                  95

Arg Gly Thr Leu Leu Val Leu Glu Gly Pro Gly Thr Ser Gln Arg Gln
            100                 105                 110

Phe Glu Ile Val Ser Asn Gly Pro Gly Asp Thr Leu Asp Leu Asn Tyr
        115                 120                 125

Trp Val Glu Gly Asn Gln His Thr Asn Phe Leu Glu Asp Val Gly Leu
    130                 135                 140

Ala Asp Ser Gln Trp Lys Asn Val Thr Val Gln Val Ala Ser Asp Thr
145                 150                 155                 160

Tyr Ser Leu Tyr Val Gly Cys Asp Leu Ile Asp Ser Val Thr Leu Glu
                165                 170                 175

Glu Pro Phe Tyr Glu Gln Leu Glu Val Asp Arg Ser Arg Met Tyr Val
            180                 185                 190
```

```
Ala Lys Gly Ala Ser Arg Glu Ser His Phe Arg Gly Leu Gln Asn
            195                 200                 205
Val His Leu Val Phe Ala Asp Ser Val Glu Asp Ile Leu Ser Lys Lys
    210                 215                 220
Gly Cys Gln His Ser Gln Gly Ala Glu Val Asn Thr Ile Ser Glu His
225                 230                 235                 240
Thr Glu Thr Leu His Leu Ser Pro His Ile Thr Thr Asp Leu Val Val
                245                 250                 255
Gln Gly Val Glu Lys Ala Gln Glu Val Cys Thr His Ser Glu Glu
            260                 265                 270
Leu Ser Asn Met Met Asn Glu Leu Ser Gly Leu His Val Met Val Asn
            275                 280                 285
Gln Leu Ser Lys Asn Leu Glu Arg Val Ser Ser Asp Asn Gln Phe Leu
    290                 295                 300
Leu Glu Leu Ile Gly Gly Pro Leu Lys Thr Arg Asn Met Ser Ala Cys
305                 310                 315                 320
Val Gln Glu Gly Arg Ile Phe Ala Glu Asn Glu Thr Trp Val Val Asp
                325                 330                 335
Ser Cys Thr Thr Cys Thr Cys Lys Lys Phe Lys Thr Val Cys His Gln
            340                 345                 350
Ile Thr Cys Ser Pro Ala Thr Cys Ala Asn Pro Ser Phe Val Glu Gly
    355                 360                 365
Glu Cys Cys Pro Ser Cys Ser His Ser Ala Asp Ser Asp Glu Gly Trp
370                 375                 380
Ser Pro Trp Ala Glu Trp Thr Glu Cys Ser Val Thr Cys Gly Ser Gly
385                 390                 395                 400
Thr Gln Gln Arg Gly Arg Ser Cys Asp Val Thr Ser Asn Thr Cys Leu
                405                 410                 415
Gly Pro Ser Ile Gln Thr Arg Thr Cys Ser Leu Gly Lys Cys Asp Thr
            420                 425                 430
Arg Ile Arg Gln Asn Gly Gly Trp Ser His Trp Ser Pro Trp Ser Ser
    435                 440                 445
Cys Ser Val Thr Cys Gly Val Gly Asn Val Thr Arg Ile Arg Leu Cys
450                 455                 460
Asn Ser Pro Val Pro Gln Met Gly Gly Lys Asn Cys Lys Gly Ser Gly
465                 470                 475                 480
Arg Glu Thr Lys Pro Cys Gln Arg Asp Pro Cys Pro Ile Asp Gly Arg
                485                 490                 495
Trp Ser Pro Trp Ser Pro Trp Ser Ala Cys Thr Val Thr Cys Ala Gly
            500                 505                 510
Gly Ile Arg Glu Arg Ser Arg Val Cys Asn Ser Pro Glu Pro Gln Tyr
    515                 520                 525
Gly Gly Lys Asp Cys Val Gly Asp Val Thr Glu His Gln Met Cys Asn
    530                 535                 540
Lys Arg Ser Cys Pro Ile Asp Gly Cys Leu Ser Asn Pro Cys Phe Pro
545                 550                 555                 560
Gly Ala Lys Cys Asn Ser Phe Pro Asp Gly Ser Trp Ser Cys Gly Ser
                565                 570                 575
Cys Pro Val Gly Phe Leu Gly Asn Gly Thr His Cys Glu Asp Leu Asp
            580                 585                 590
Glu Cys Ala Val Val Thr Asp Ile Cys Phe Ser Thr Asn Lys Ala Pro
    595                 600                 605
```

-continued

```
Arg Cys Val Asn Thr Asn Pro Gly Phe His Cys Leu Pro Cys Pro Pro
610                 615                 620
Arg Tyr Lys Gly Asn Gln Pro Phe Gly Val Gly Leu Glu Asp Ala Arg
625                 630                 635                 640
Thr Glu Lys Gln Val Cys Glu Pro Glu Asn Pro Cys Lys Asp Lys Thr
                645                 650                 655
His Ser Cys His Lys Asn Ala Glu Cys Ile Tyr Leu Gly His Phe Ser
                660                 665                 670
Asp Pro Met Tyr Lys Cys Glu Cys Gln Ile Gly Tyr Ala Gly Asp Gly
        675                 680                 685
Leu Ile Cys Gly Glu Asp Ser Asp Leu Asp Gly Trp Pro Asn Asn Asn
690                 695                 700
Leu Val Cys Ala Thr Asn Ala Thr Tyr His Cys Ile Lys Asp Asn Cys
705                 710                 715                 720
Pro Lys Leu Pro Asn Ser Gly Gln Glu Asp Phe Asp Lys Asp Gly Ile
                725                 730                 735
Gly Asp Ala Cys Asp Glu Asp Asp Asn Asp Gly Val Ser Asp Glu
                740                 745                 750
Lys Asp Asn Cys Gln Leu Leu Phe Asn Pro Arg Gln Leu Asp Tyr Asp
                755                 760                 765
Lys Asp Glu Val Gly Asp Arg Cys Asp Asn Cys Pro Tyr Val His Asn
770                 775                 780
Pro Ala Gln Ile Asp Thr Asp Asn Asn Gly Glu Gly Asp Ala Cys Ser
785                 790                 795                 800
Val Asp Ile Asp Gly Asp Asp Val Phe Asn Glu Arg Asp Asn Cys Pro
                805                 810                 815
Tyr Val Tyr Asn Thr Asp Gln Arg Asp Thr Asp Gly Asp Gly Val Gly
                820                 825                 830
Asp His Cys Asp Asn Cys Pro Leu Met His Asn Pro Asp Gln Ile Asp
                835                 840                 845
Gln Asp Asn Asp Leu Val Gly Asp Gln Cys Asp Asn Asn Glu Asp Ile
850                 855                 860
Asp Asp Asp Gly His Gln Asn Asn Gln Asp Asn Cys Pro Tyr Ile Ser
865                 870                 875                 880
Asn Ser Asn Gln Ala Asp His Asp Asn Asp Gly Lys Gly Asp Ala Cys
                885                 890                 895
Asp Ser Asp Asp Asp Asn Asp Gly Val Pro Asp Asp Arg Asp Asn Cys
                900                 905                 910
Arg Leu Val Phe Asn Pro Asp Gln Glu Asp Ser Asp Gly Asp Gly Arg
                915                 920                 925
Gly Asp Ile Cys Lys Asp Asp Phe Asp Asn Asp Asn Val Pro Asp Ile
930                 935                 940
Asp Asp Val Cys Pro Glu Asn Asn Ala Ile Thr Glu Thr Asp Phe Arg
945                 950                 955                 960
Asn Phe Gln Met Val Pro Leu Asp Pro Lys Gly Thr Thr Gln Ile Asp
                965                 970                 975
Pro Asn Trp Val Ile Arg His Gln Gly Lys Glu Leu Val Gln Thr Ala
                980                 985                 990
Asn Ser Asp Pro Gly Ile Ala Val Gly Phe Asp Glu Phe Gly Ser Val
                995                 1000                1005
Asp Phe Ser Gly Thr Phe Tyr Val Asn Thr Asp Arg Asp Asp Asp Tyr
1010                1015                1020
```

Ala Gly Phe Val Phe Gly Tyr Gln Ser Ser Ser Arg Phe Tyr Val Val
1025                1030                1035                1040

Met Trp Lys Gln Val Thr Gln Thr Tyr Trp Glu Asp Lys Pro Ser Arg
            1045                1050                1055

Ala Tyr Gly Tyr Ser Gly Val Ser Leu Lys Val Val Asn Ser Thr Thr
            1060                1065                1070

Gly Thr Gly Glu His Leu Arg Asn Ala Leu Trp His Thr Gly Asn Thr
            1075                1080                1085

Glu Gly Gln Val Arg Thr Leu Trp His Asp Pro Lys Asn Ile Gly Trp
            1090                1095                1100

Lys Asp Tyr Thr Ala Tyr Arg Trp His Leu Ile His Arg Pro Lys Thr
1105                1110                1115                1120

Gly Tyr Met Arg Val Leu Val His Glu Gly Lys Gln Val Met Ala Asp
            1125                1130                1135

Ser Gly Pro Ile Tyr Asp Gln Thr Tyr Ala Gly Gly Arg Leu Gly Leu
            1140                1145                1150

Phe Val Phe Ser Gln Glu Met Val Tyr Phe Ser Asp Leu Lys Tyr Glu
            1155                1160                1165

Cys Arg Asp Ala
    1170

<210> SEQ ID NO 3
<211> LENGTH: 1170
<212> TYPE: PRT
<213> ORGANISM: Homo sapiens

<400> SEQUENCE: 3

Met Gly Leu Ala Trp Gly Leu Gly Val Leu Phe Leu Met His Val Cys
  1               5                  10                  15

Gly Thr Asn Arg Ile Pro Glu Ser Gly Gly Asp Asn Ser Val Phe Asp
                20                  25                  30

Ile Phe Glu Leu Thr Gly Ala Ala Arg Lys Gly Ser Gly Arg Arg Leu
            35                  40                  45

Val Lys Gly Pro Asp Pro Ser Ser Pro Ala Phe Arg Ile Glu Asp Ala
    50                  55                  60

Asn Leu Ile Pro Pro Val Pro Asp Asp Lys Phe Gln Asp Leu Val Asp
65                  70                  75                  80

Ala Val Arg Ala Glu Lys Gly Phe Leu Leu Leu Ala Ser Leu Arg Gln
                85                  90                  95

Met Lys Lys Thr Arg Gly Thr Leu Leu Ala Leu Glu Arg Lys Asp His
            100                 105                 110

Ser Gly Gln Val Phe Ser Val Val Ser Asn Gly Lys Ala Gly Thr Leu
        115                 120                 125

Asp Leu Ser Leu Thr Val Gln Gly Lys Gln His Val Val Ser Val Glu
    130                 135                 140

Glu Ala Leu Leu Ala Thr Gly Gln Trp Lys Ser Ile Thr Leu Phe Val
145                 150                 155                 160

Gln Glu Asp Arg Ala Gln Leu Tyr Ile Asp Cys Glu Lys Met Glu Asn
                165                 170                 175

Ala Glu Leu Asp Val Pro Ile Gln Ser Val Phe Thr Arg Asp Leu Ala
            180                 185                 190

Ser Ile Ala Arg Leu Arg Ile Ala Lys Gly Gly Val Asn Asp Asn Phe
        195                 200                 205

Gln Gly Val Leu Gln Asn Val Arg Phe Val Phe Gly Thr Thr Pro Glu
    210                 215                 220

-continued

```
Asp Ile Leu Arg Asn Lys Gly Cys Ser Ser Thr Ser Val Leu Leu
225                 230                 235                 240

Thr Leu Asp Asn Val Val Asn Gly Ser Ser Pro Ala Ile Arg Thr
            245                 250                 255

Asn Tyr Ile Gly His Lys Thr Lys Asp Leu Gln Ala Ile Cys Gly Ile
                260                 265                 270

Ser Cys Asp Glu Leu Ser Ser Met Val Leu Glu Leu Arg Gly Leu Arg
            275                 280                 285

Thr Ile Val Thr Thr Leu Gln Asp Ser Ile Arg Lys Val Thr Glu Glu
        290                 295                 300

Asn Lys Glu Leu Ala Asn Glu Leu Arg Arg Pro Pro Leu Cys Tyr His
305                 310                 315                 320

Asn Gly Val Gln Tyr Arg Asn Asn Glu Glu Trp Thr Val Asp Ser Cys
                325                 330                 335

Thr Glu Cys His Cys Gln Asn Ser Val Thr Ile Cys Lys Lys Val Ser
            340                 345                 350

Cys Pro Ile Met Pro Cys Ser Asn Ala Thr Val Pro Asp Gly Glu Cys
        355                 360                 365

Cys Pro Arg Cys Trp Pro Ser Asp Ser Ala Asp Asp Gly Trp Ser Pro
370                 375                 380

Trp Ser Glu Trp Thr Ser Cys Ser Thr Ser Cys Gly Asn Gly Ile Gln
385                 390                 395                 400

Gln Arg Gly Arg Ser Cys Asp Ser Leu Asn Asn Arg Cys Glu Gly Ser
                405                 410                 415

Ser Val Gln Thr Arg Thr Cys His Ile Gln Glu Cys Asp Lys Arg Phe
            420                 425                 430

Lys Gln Asp Gly Gly Trp Ser His Trp Ser Pro Trp Ser Ser Cys Ser
        435                 440                 445

Val Thr Cys Gly Asp Gly Val Ile Thr Arg Ile Arg Leu Cys Asn Ser
450                 455                 460

Pro Ser Pro Gln Met Asn Gly Lys Pro Cys Glu Gly Glu Ala Arg Glu
465                 470                 475                 480

Thr Lys Ala Cys Lys Lys Asp Ala Cys Pro Ile Asn Gly Gly Trp Gly
                485                 490                 495

Pro Trp Ser Pro Trp Asp Ile Cys Ser Val Thr Cys Gly Gly Gly Val
            500                 505                 510

Gln Lys Arg Ser Arg Leu Cys Asn Asn Pro Thr Pro Gln Phe Gly Gly
        515                 520                 525

Lys Asp Cys Val Gly Asp Val Thr Glu Asn Gln Ile Cys Asn Lys Gln
530                 535                 540

Asp Cys Pro Ile Asp Gly Cys Leu Ser Asn Pro Cys Phe Ala Gly Val
545                 550                 555                 560

Lys Cys Thr Ser Tyr Pro Asp Gly Ser Trp Lys Cys Gly Ala Cys Pro
                565                 570                 575

Pro Gly Tyr Ser Gly Asn Gly Ile Gln Cys Thr Asp Val Asp Glu Cys
            580                 585                 590

Lys Glu Val Pro Asp Ala Cys Phe Asn His Asn Gly Glu His Arg Cys
        595                 600                 605

Glu Asn Thr Asp Pro Gly Tyr Asn Cys Leu Pro Cys Pro Pro Arg Phe
610                 615                 620

Thr Gly Ser Gln Pro Phe Gly Gln Gly Val Glu His Ala Thr Ala Asn
625                 630                 635                 640
```

-continued

Lys Gln Val Cys Lys Pro Arg Asn Pro Cys Thr Asp Gly Thr His Asp
                645                 650                 655

Cys Asn Lys Asn Ala Lys Cys Asn Tyr Leu Gly His Tyr Ser Asp Pro
            660                 665                 670

Met Tyr Arg Cys Glu Cys Lys Pro Gly Tyr Ala Gly Asn Gly Ile Ile
        675                 680                 685

Cys Gly Glu Asp Thr Asp Leu Asp Gly Trp Pro Asn Glu Asn Leu Val
    690                 695                 700

Cys Val Ala Asn Ala Thr Tyr His Cys Lys Lys Asp Asn Cys Pro Asn
705                 710                 715                 720

Leu Pro Asn Ser Gly Gln Glu Asp Tyr Asp Lys Asp Gly Ile Gly Asp
            725                 730                 735

Ala Cys Asp Asp Asp Asp Asn Asp Lys Ile Pro Asp Asp Arg Asp
        740                 745                 750

Asn Cys Pro Phe His Tyr Asn Pro Ala Gln Tyr Asp Tyr Asp Arg Asp
    755                 760                 765

Asp Val Gly Asp Arg Cys Asp Asn Cys Pro Tyr Asn His Asn Pro Asp
770                 775                 780

Gln Ala Asp Thr Asp Asn Asn Gly Glu Gly Asp Ala Cys Ala Ala Asp
785                 790                 795                 800

Ile Asp Gly Asp Gly Ile Leu Asn Glu Arg Asp Asn Cys Gln Tyr Val
            805                 810                 815

Tyr Asn Val Asp Gln Arg Asp Thr Asp Met Asp Gly Val Gly Asp Gln
        820                 825                 830

Cys Asp Asn Cys Pro Leu Glu His Asn Pro Asp Gln Leu Asp Ser Asp
    835                 840                 845

Ser Asp Arg Ile Gly Asp Thr Cys Asp Asn Asn Gln Asp Ile Asp Glu
850                 855                 860

Asp Gly His Gln Asn Asn Leu Asp Asn Cys Pro Tyr Val Pro Asn Ala
865                 870                 875                 880

Asn Gln Ala Asp His Asp Lys Asp Gly Lys Gly Asp Ala Cys Asp His
            885                 890                 895

Asp Asp Asp Asn Asp Gly Ile Pro Asp Asp Lys Asp Asn Cys Arg Leu
        900                 905                 910

Val Pro Asn Pro Asp Gln Lys Asp Ser Asp Gly Asp Gly Arg Gly Asp
    915                 920                 925

Ala Cys Lys Asp Asp Phe Asp His Asp Ser Val Pro Asp Ile Asp Asp
    930                 935                 940

Ile Cys Pro Glu Asn Val Asp Ile Ser Glu Thr Asp Phe Arg Arg Phe
945                 950                 955                 960

Gln Met Ile Pro Leu Asp Pro Lys Gly Thr Ser Gln Asn Asp Pro Asn
            965                 970                 975

Trp Val Val Arg His Gln Gly Lys Glu Leu Val Gln Thr Val Asn Cys
        980                 985                 990

Asp Pro Gly Leu Ala Val Gly Tyr Asp Glu Phe Asn Ala Val Asp Phe
    995                 1000                1005

Ser Gly Thr Phe Phe Ile Asn Thr Glu Arg Asp Asp Asp Tyr Ala Gly
    1010                1015                1020

Phe Val Phe Gly Tyr Gln Ser Ser Ser Arg Phe Tyr Val Val Met Trp
1025                1030                1035                1040

Lys Gln Val Thr Gln Ser Tyr Trp Asp Thr Asn Pro Thr Arg Ala Gln
            1045                1050                1055

```
Gly Tyr Ser Gly Leu Ser Val Lys Val Val Asn Ser Thr Thr Gly Pro
            1060                1065                1070

Gly Glu His Leu Arg Asn Ala Leu Trp His Thr Gly Asn Thr Pro Gly
        1075                1080                1085

Gln Val Arg Thr Leu Trp His Asp Pro Arg His Ile Gly Trp Lys Asp
        1090                1095                1100

Phe Thr Ala Tyr Arg Trp Arg Leu Ser His Arg Pro Lys Thr Gly Phe
1105                1110                1115                1120

Ile Arg Val Val Met Tyr Glu Gly Lys Lys Ile Met Ala Asp Ser Gly
                1125                1130                1135

Pro Ile Tyr Asp Lys Thr Tyr Ala Gly Gly Arg Leu Gly Leu Phe Val
                1140                1145                1150

Phe Ser Gln Glu Met Val Phe Phe Ser Asp Leu Lys Tyr Glu Cys Arg
        1155                1160                1165

Asp Pro
    1170

<210> SEQ ID NO 4
<211> LENGTH: 1171
<212> TYPE: PRT
<213> ORGANISM: Mus musculus

<400> SEQUENCE: 4

Met Glu Leu Leu Arg Gly Leu Gly Val Leu Phe Leu Leu His Met Cys
1               5                   10                  15

Gly Ser Asn Arg Ile Pro Glu Ser Gly Gly Asp Asn Gly Val Phe Asp
            20                  25                  30

Ile Phe Glu Leu Ile Gly Gly Ala Arg Arg Gly Pro Gly Arg Arg Leu
        35                  40                  45

Val Lys Gly Gln Asp Leu Ser Ser Pro Ala Phe Arg Ile Glu Asn Ala
    50                  55                  60

Asn Leu Ile Pro Ala Val Pro Asp Asp Lys Phe Gln Asp Leu Leu Asp
65                  70                  75                  80

Ala Val Trp Ala Asp Lys Gly Phe Ile Phe Leu Ala Ser Leu Arg Gln
                85                  90                  95

Met Lys Lys Thr Arg Gly Thr Leu Leu Ala Val Glu Arg Lys Asp Asn
            100                 105                 110

Thr Gly Gln Ile Phe Ser Val Val Ser Asn Gly Lys Ala Gly Thr Leu
        115                 120                 125

Asp Leu Ser Leu Ser Leu Pro Gly Lys Gln Gln Val Val Ser Val Glu
    130                 135                 140

Glu Ala Leu Leu Ala Thr Gly Gln Trp Lys Ser Ile Thr Leu Phe Val
145                 150                 155                 160

Gln Glu Asp Arg Ala Gln Leu Tyr Ile Asp Cys Asp Lys Met Glu Ser
                165                 170                 175

Ala Glu Leu Asp Val Pro Ile Gln Ser Ile Phe Thr Arg Asp Leu Ala
            180                 185                 190

Ser Val Ala Arg Leu Arg Val Ala Lys Gly Asp Val Asn Asp Asn Phe
        195                 200                 205

Gln Gly Val Leu Gln Asn Val Arg Phe Val Phe Gly Thr Thr Pro Glu
    210                 215                 220

Asp Ile Leu Arg Asn Lys Gly Cys Ser Ser Ser Ala Thr Asn Val Leu
225                 230                 235                 240

Leu Thr Leu Asp Asn Asn Val Val Asn Gly Ser Ser Pro Ala Ile Arg
                245                 250                 255
```

```
Thr Asn Tyr Ile Gly His Lys Thr Lys Asp Leu Gln Ala Ile Cys Gly
                260                 265                 270

Leu Ser Cys Asp Glu Leu Ser Ser Met Val Leu Glu Leu Lys Gly Leu
            275                 280                 285

Arg Thr Ile Val Thr Thr Leu Gln Asp Ser Ile Arg Lys Val Thr Glu
        290                 295                 300

Glu Asn Arg Glu Leu Val Ser Glu Leu Lys Arg Pro Pro Leu Cys Phe
305                 310                 315                 320

His Asn Gly Val Gln Tyr Lys Asn Asn Glu Glu Trp Thr Val Asp Ser
                325                 330                 335

Cys Thr Glu Cys His Cys Gln Asn Ser Val Thr Ile Cys Lys Lys Val
            340                 345                 350

Ser Cys Pro Ile Met Pro Cys Ser Asn Ala Thr Val Pro Asp Gly Glu
        355                 360                 365

Cys Cys Pro Arg Cys Trp Pro Ser Asp Ser Ala Asp Asp Gly Trp Ser
370                 375                 380

Pro Trp Ser Glu Trp Thr Ser Cys Ser Ala Thr Cys Gly Asn Gly Ile
385                 390                 395                 400

Gln Gln Arg Gly Arg Ser Cys Asp Ser Leu Asn Asn Arg Cys Glu Gly
                405                 410                 415

Ser Ser Val Gln Thr Arg Thr Cys His Ile Gln Glu Cys Asp Lys Arg
            420                 425                 430

Phe Lys Gln Asp Gly Gly Trp Ser His Trp Ser Pro Trp Ser Ser Cys
        435                 440                 445

Ser Val Thr Cys Gly Asp Gly Val Ile Thr Arg Ile Arg Leu Cys Asn
450                 455                 460

Ser Pro Ser Pro Gln Met Asn Gly Lys Pro Cys Glu Gly Glu Ala Arg
465                 470                 475                 480

Glu Thr Lys Ala Cys Lys Lys Asp Ala Cys Pro Ile Asn Gly Gly Trp
                485                 490                 495

Gly Pro Trp Ser Pro Trp Asp Ile Cys Ser Val Thr Cys Gly Gly Gly
            500                 505                 510

Val Gln Arg Arg Ser Arg Leu Cys Asn Asn Pro Thr Pro Gln Phe Gly
        515                 520                 525

Gly Lys Asp Cys Val Gly Asp Val Thr Glu Asn Gln Val Cys Asn Lys
530                 535                 540

Gln Asp Cys Pro Ile Asp Gly Cys Leu Ser Asn Pro Cys Phe Ala Gly
545                 550                 555                 560

Ala Lys Cys Thr Ser Tyr Pro Asp Gly Ser Trp Lys Cys Gly Ala Cys
                565                 570                 575

Pro Pro Gly Tyr Ser Gly Asn Gly Ile Gln Cys Lys Asp Val Asp Glu
            580                 585                 590

Cys Lys Glu Val Pro Asp Ala Cys Phe Asn His Asn Gly Glu His Arg
        595                 600                 605

Cys Lys Asn Thr Asp Pro Gly Tyr Asn Cys Leu Pro Cys Pro Pro Arg
610                 615                 620

Phe Thr Gly Ser Gln Pro Phe Gly Arg Gly Val Glu His Ala Met Ala
625                 630                 635                 640

Asn Lys Gln Val Cys Lys Pro Arg Asn Pro Cys Thr Asp Gly Thr His
                645                 650                 655

Asp Cys Asn Lys Asn Ala Lys Cys Asn Tyr Leu Gly His Tyr Ser Asp
            660                 665                 670
```

```
Pro Met Tyr Arg Cys Glu Cys Lys Pro Gly Tyr Ala Gly Asn Gly Ile
            675                 680                 685
Ile Cys Gly Glu Asp Thr Asp Leu Asp Gly Trp Pro Asn Glu Asn Leu
690                 695                 700
Val Cys Val Ala Asn Ala Thr Tyr His Cys Lys Lys Asp Asn Cys Pro
705                 710                 715                 720
Asn Leu Pro Asn Ser Gly Gln Glu Asp Tyr Asp Lys Asp Gly Ile Gly
            725                 730                 735
Asp Ala Cys Asp Asp Asp Asp Asn Asp Lys Ile Pro Asp Asp Arg
            740                 745                 750
Asp Asn Cys Pro Phe His Tyr Asn Pro Ala Gln Tyr Asp Tyr Asp Arg
            755                 760                 765
Asp Asp Val Gly Asp Arg Cys Asp Asn Cys Pro Tyr Asn His Asn Pro
770                 775                 780
Asp Gln Ala Asp Thr Asp Lys Asn Gly Glu Gly Asp Ala Cys Ala Val
785                 790                 795                 800
Asp Ile Asp Gly Asp Gly Ile Leu Asn Glu Arg Asp Asn Cys Gln Tyr
            805                 810                 815
Val Tyr Asn Val Asp Gln Arg Asp Thr Asp Met Asp Gly Val Gly Asp
            820                 825                 830
Gln Cys Asp Asn Cys Pro Leu Glu His Asn Pro Asp Gln Leu Asp Ser
            835                 840                 845
Asp Ser Asp Leu Ile Gly Asp Thr Cys Asp Asn Asn Gln Asp Ile Asp
            850                 855                 860
Glu Asp Gly His Gln Asn Asn Leu Asp Asn Cys Pro Tyr Val Pro Asn
865                 870                 875                 880
Ala Asn Gln Ala Asp His Asp Lys Asp Gly Lys Gly Asp Ala Cys Asp
            885                 890                 895
His Asp Asp Asp Asn Asp Gly Ile Pro Asp Asp Arg Asp Asn Cys Arg
                900                 905                 910
Leu Val Pro Asn Pro Asp Gln Lys Asp Ser Asp Gly Asp Gly Arg Gly
            915                 920                 925
Asp Ala Cys Lys Asp Asp Phe Asp His Asp Asn Val Pro Asp Ile Asp
            930                 935                 940
Asp Ile Cys Pro Glu Asn Phe Asp Ile Ser Glu Thr Asp Phe Arg Gln
945                 950                 955                 960
Phe Gln Met Ile Pro Leu Asp Pro Lys Gly Thr Ser Gln Asn Asp Pro
            965                 970                 975
Asn Trp Val Val Arg His Gln Gly Lys Glu Leu Val Gln Thr Val Asn
            980                 985                 990
Cys Asp Pro Gly Leu Ala Val Gly Tyr Asp Glu Phe Asn Ala Val Asp
            995                 1000                1005
Phe Ser Gly Thr Phe Pro Ile Asn Thr Glu Arg Asp Asp Asp Tyr Ala
            1010                1015                1020
Gly Phe Val Phe Gly Tyr Gln Ser Ser Arg Phe Tyr Val Val Met
1025                1030                1035                1040
Trp Lys Gln Val Thr Gln Ser Tyr Trp Asp Thr Asn Pro Thr Arg Ala
            1045                1050                1055
Gln Gly Tyr Ser Gly Leu Ser Val Lys Val Val Asn Ser Thr Thr Gly
            1060                1065                1070
Pro Gly Glu His Leu Arg Asn Ala Leu Trp His Thr Gly Asn Thr Pro
            1075                1080                1085
```

-continued

```
Gly Gln Val Arg Thr Leu Trp His Asp Pro Arg His Ile Gly Trp Lys
    1090                1095                1100

Asp Phe Thr Ala Tyr Arg Trp Arg Leu Ser His Arg Pro Lys Thr Gly
1105                1110                1115                1120

Tyr Ile Arg Val Val Met Tyr Glu Gly Lys Lys Ile Met Ala Asp Ser
                1125                1130                1135

Gly Pro Ile Tyr Asp Lys Thr Tyr Ala Gly Gly Arg Leu Gly Leu Phe
                1140                1145                1150

Val Phe Ser Gln Glu Met Val Phe Phe Ser Asp Met Lys Tyr Glu Cys
                1155                1160                1165

Arg Asp Ser
    1170

<210> SEQ ID NO 5
<211> LENGTH: 288
<212> TYPE: PRT
<213> ORGANISM: Homo sapiens

<400> SEQUENCE: 5

Met Ser Leu Val Leu Leu Ser Leu Ala Ala Leu Cys Arg Ser Ala Val
1               5                   10                  15

Pro Arg Glu Pro Thr Val Gln Cys Gly Ser Glu Thr Gly Pro Ser Pro
                20                  25                  30

Glu Trp Met Leu Gln His Asp Leu Ile Pro Gly Asp Leu Arg Asp Leu
            35                  40                  45

Arg Val Glu Pro Val Thr Thr Ser Val Ala Thr Gly Asp Tyr Ser Ile
        50                  55                  60

Leu Met Asn Val Ser Trp Val Leu Arg Ala Asp Ala Ser Ile Arg Leu
65                  70                  75                  80

Leu Lys Ala Thr Lys Ile Cys Val Thr Gly Lys Ser Asn Phe Gln Ser
                85                  90                  95

Tyr Ser Cys Val Arg Cys Asn Tyr Thr Glu Ala Phe Gln Thr Gln Thr
            100                 105                 110

Arg Pro Ser Gly Gly Lys Trp Thr Phe Ser Tyr Ile Gly Phe Pro Val
        115                 120                 125

Glu Leu Asn Thr Val Tyr Phe Ile Gly Ala His Asn Ile Pro Asn Ala
130                 135                 140

Asn Met Asn Glu Asp Gly Pro Ser Met Ser Val Asn Phe Thr Ser Pro
145                 150                 155                 160

Gly Cys Leu Asp His Ile Met Lys Tyr Lys Lys Cys Val Lys Ala
                165                 170                 175

Gly Ser Leu Trp Asp Pro Asn Ile Thr Ala Cys Lys Lys Asn Glu Glu
            180                 185                 190

Thr Val Glu Val Asn Phe Thr Thr Thr Pro Leu Gly Asn Arg Tyr Met
        195                 200                 205

Ala Leu Ile Gln His Ser Thr Ile Ile Gly Phe Ser Gln Val Phe Glu
    210                 215                 220

Pro His Gln Lys Lys Gln Thr Arg Ala Ser Val Val Ile Pro Val Thr
225                 230                 235                 240

Gly Asp Ser Glu Gly Ala Thr Val Gln Val Lys Phe Ser Glu Leu Leu
                245                 250                 255

Trp Gly Gly Lys Gly His Arg Arg Leu Phe His His Ser Leu Leu Leu
            260                 265                 270

Arg Met Ser Ser Leu Leu Ser Asn Ala Leu Leu Pro Ala Asp Thr Ser
        275                 280                 285
```

<210> SEQ ID NO 6
<211> LENGTH: 499
<212> TYPE: PRT
<213> ORGANISM: Mus musculus

<400> SEQUENCE: 6

```
Met Leu Leu Val Leu Ile Leu Ala Ala Ser Cys Arg Ser Ala Leu
 1               5                  10                  15

Pro Arg Glu Pro Thr Ile Gln Cys Gly Ser Glu Thr Gly Pro Ser Pro
             20                  25                  30

Glu Trp Met Val Gln His Thr Leu Thr Pro Gly Asp Leu Arg Asp Leu
         35                  40                  45

Gln Val Glu Leu Val Lys Thr Ser Val Ala Ala Glu Glu Phe Ser Ile
     50                  55                  60

Leu Met Asn Ile Ser Trp Ile Leu Arg Ala Asp Ala Ser Ile Arg Leu
 65                  70                  75                  80

Leu Lys Ala Thr Lys Ile Cys Val Ser Gly Lys Asn Asn Met Asn Ser
                 85                  90                  95

Tyr Ser Cys Val Arg Cys Asn Tyr Thr Glu Ala Phe Gln Ser Gln Thr
            100                 105                 110

Arg Pro Ser Gly Gly Lys Trp Thr Phe Ser Tyr Val Gly Phe Pro Val
        115                 120                 125

Glu Leu Ser Thr Leu Tyr Leu Ile Ser Ala His Asn Ile Pro Asn Ala
    130                 135                 140

Asn Met Asn Glu Asp Ser Pro Ser Leu Ser Val Asn Phe Thr Ser Pro
145                 150                 155                 160

Gly Cys Leu Asn His Val Met Lys Tyr Lys Lys Gln Cys Thr Glu Ala
                165                 170                 175

Gly Ser Leu Trp Asp Pro Asp Ile Thr Ala Cys Lys Lys Asn Glu Lys
            180                 185                 190

Met Val Glu Val Asn Phe Thr Thr Asn Pro Leu Gly Asn Arg Tyr Thr
        195                 200                 205

Ile Leu Ile Gln Arg Asp Thr Thr Leu Gly Phe Ser Arg Val Leu Glu
    210                 215                 220

Asn Lys Leu Met Arg Thr Ser Val Ala Ile Pro Val Thr Glu Glu Ser
225                 230                 235                 240

Glu Gly Ala Val Val Gln Leu Thr Pro Tyr Leu His Thr Cys Gly Asn
                245                 250                 255

Asp Cys Ile Arg Arg Glu Gly Thr Val Val Leu Cys Ser Glu Thr Ser
            260                 265                 270

Ala Pro Ile Pro Pro Asp Asp Asn Arg Arg Met Leu Gly Gly Trp Leu
        275                 280                 285

Pro Leu Phe Leu Val Leu Leu Val Ala Val Trp Val Leu Ala Ala Gly
    290                 295                 300

Ile Tyr Leu Thr Trp Arg Gln Gly Arg Ser Thr Lys Thr Ser Phe Pro
305                 310                 315                 320

Ile Ser Thr Met Leu Leu Pro Leu Ile Lys Val Leu Val Val Tyr Pro
                325                 330                 335

Ser Glu Ile Cys Phe His His Thr Val Cys Arg Phe Thr Asp Phe Leu
            340                 345                 350

Gln Asn Tyr Cys Arg Ser Glu Val Ile Leu Glu Lys Trp Gln Lys Lys
        355                 360                 365
```

```
Lys Ile Ala Glu Met Gly Pro Val Gln Trp Leu Thr Thr Gln Lys Gln
    370                 375                 380

Ala Ala Asp Lys Val Val Phe Leu Leu Pro Ser Asp Val Pro Thr Leu
385                 390                 395                 400

Cys Asp Ser Ala Cys Gly His Asn Glu Gly Ser Ala Arg Glu Asn Ser
                405                 410                 415

Gln Asp Leu Phe Pro Leu Ala Phe Asn Leu Phe Cys Ser Asp Phe Ser
            420                 425                 430

Ser Gln Thr His Leu His Lys Tyr Leu Val Val Tyr Leu Gly Gly Ala
        435                 440                 445

Asp Leu Lys Gly Asp Tyr Asn Ala Leu Ser Val Cys Pro Gln Tyr His
    450                 455                 460

Leu Met Lys Asp Ala Thr Ala Phe His Thr Glu Leu Leu Lys Ala Thr
465                 470                 475                 480

Gln Ser Met Ser Val Lys Lys Arg Ser Gln Ala Cys His Asp Ser Cys
                485                 490                 495

Ser Pro Leu

<210> SEQ ID NO 7
<211> LENGTH: 208
<212> TYPE: PRT
<213> ORGANISM: Homo sapiens

<400> SEQUENCE: 7

Met Lys Leu Leu Pro Ser Val Val Leu Lys Leu Phe Leu Ala Ala Val
  1               5                  10                  15

Leu Ser Ala Leu Val Thr Gly Glu Ser Leu Glu Arg Leu Arg Arg Gly
                20                  25                  30

Leu Ala Ala Gly Thr Ser Asn Pro Asp Pro Pro Thr Val Ser Thr Asp
            35                  40                  45

Gln Leu Leu Pro Leu Gly Gly Gly Arg Asp Arg Lys Val Arg Asp Leu
        50                  55                  60

Gln Glu Ala Asp Leu Asp Leu Leu Arg Val Thr Leu Ser Ser Lys Pro
 65                  70                  75                  80

Gln Ala Leu Ala Thr Pro Asn Lys Glu Glu His Gly Lys Arg Lys Lys
                 85                  90                  95

Lys Gly Lys Gly Leu Gly Lys Lys Arg Asp Pro Cys Leu Arg Lys Tyr
            100                 105                 110

Lys Asp Phe Cys Ile His Gly Glu Cys Lys Tyr Val Lys Glu Leu Arg
        115                 120                 125

Ala Pro Ser Cys Ile Cys His Pro Gly Tyr His Gly Glu Arg Cys His
    130                 135                 140

Gly Leu Ser Leu Pro Val Glu Asn Arg Leu Tyr Thr Tyr Asp His Thr
145                 150                 155                 160

Thr Ile Leu Ala Val Val Ala Val Val Leu Ser Ser Val Cys Leu Leu
                165                 170                 175

Val Ile Val Gly Leu Leu Met Phe Arg Tyr His Arg Arg Gly Gly Tyr
            180                 185                 190

Asp Val Glu Asn Glu Glu Lys Val Lys Leu Gly Met Thr Asn Ser His
        195                 200                 205

<210> SEQ ID NO 8
<211> LENGTH: 208
<212> TYPE: PRT
<213> ORGANISM: Mus musculus
```

<400> SEQUENCE: 8

```
Met Lys Leu Leu Pro Ser Val Met Leu Lys Leu Phe Leu Ala Ala Val
 1               5                  10                  15

Leu Ser Ala Leu Val Thr Gly Glu Ser Leu Glu Arg Leu Arg Arg Gly
            20                  25                  30

Leu Ala Ala Ala Thr Ser Asn Pro Asp Pro Thr Gly Ser Thr Asn
        35                  40                  45

Gln Leu Leu Pro Thr Gly Gly Asp Arg Ala Gln Gly Val Gln Asp Leu
    50                  55                  60

Glu Gly Thr Asp Leu Asn Leu Phe Lys Val Ala Phe Ser Ser Lys Pro
 65                  70                  75                  80

Gln Gly Leu Ala Thr Pro Ser Lys Glu Arg Asn Gly Lys Lys Lys Lys
                85                  90                  95

Lys Gly Lys Gly Leu Gly Lys Lys Arg Asp Pro Cys Leu Arg Lys Tyr
            100                 105                 110

Lys Asp Tyr Cys Ile His Gly Glu Cys Arg Tyr Leu Gln Glu Phe Arg
            115                 120                 125

Thr Pro Ser Cys Lys Cys Leu Pro Gly Tyr His Gly His Arg Cys His
        130                 135                 140

Gly Leu Thr Leu Pro Val Glu Asn Pro Leu Tyr Thr Tyr Asp His Thr
145                 150                 155                 160

Thr Val Leu Ala Val Val Ala Val Val Leu Ser Ser Val Cys Leu Leu
                165                 170                 175

Val Ile Val Gly Leu Leu Met Phe Arg Tyr His Arg Arg Gly Gly Tyr
            180                 185                 190

Asp Leu Glu Ser Glu Glu Lys Val Lys Leu Gly Val Ala Ser Ser His
            195                 200                 205
```

<210> SEQ ID NO 9
<211> LENGTH: 21
<212> TYPE: DNA
<213> ORGANISM: Artificial Sequence
<220> FEATURE:
<223> OTHER INFORMATION: Synthetic construct (Artificial DNA/RNA
      sequence: siRNA sense strand for TSP-2 mRNA)
<220> FEATURE:
<221> NAME/KEY: misc_feature
<222> LOCATION: (1)..(19)
<223> OTHER INFORMATION: RNA segment
<220> FEATURE:
<221> NAME/KEY: misc_feature
<222> LOCATION: (20)..(21)
<223> OTHER INFORMATION: DNA segment

<400> SEQUENCE: 9
cauuaagguu ccaguuauat t          21

<210> SEQ ID NO 10
<211> LENGTH: 21
<212> TYPE: DNA
<213> ORGANISM: Artificial Sequence
<220> FEATURE:
<223> OTHER INFORMATION: Synthetic construct (Artificial DNA/RNA
      Sequence: siRNA antisence strand for TSP-2 mRNA)
<220> FEATURE:
<221> NAME/KEY: misc_feature
<222> LOCATION: (1)..(19)
<223> OTHER INFORMATION: RNA segment

```
<220> FEATURE:
<221> NAME/KEY: misc_feature
<222> LOCATION: (20)..(21)
<223> OTHER INFORMATION: DNA segment

<400> SEQUENCE: 10
uauaacugga accuuaaugt t                                              21
```

METHOD OF SELECTING STEM CELLS HAVING HIGH CHONDROGENIC DIFFERENTIATION CAPABILITY

CROSS-REFERENCE TO RELATED PATENT APPLICATION

This application claims the benefit of Korean Patent Application No. 10-2010-0045128, filed on May 13, 2010, in the Korean Intellectual Property Office and U.S. Provisional Patent Application No. 61/182,484, filed on May 29, 2009, in the USPTO, the disclosure of which are incorporated herein in their entirety by reference.

BACKGROUND OF THE INVENTION

1. Field of the Invention

One or more embodiments of the present invention relate to thrombospondin 1 (TSP-1), TSP-2, interleukin 17B receptor (IL-17BR), and heparin-binding epidermal growth factor-like growth factor (HB-EGF) associated with stem cell activity, for example, activity of a mesenchymal stem cell (MSC), and use thereof.

2. Description of the Related Art

Cartilage is a kind of dense and thick connective tissue, and is composed of chondrocytes distributed in a stiff yet flexible gel-like matrix. Cartilage does not contain blood vessels, and the chondrocytes are supplied by diffusion via the matrix. Cartilage is classified into three types: hyaline cartilage (for example, cartilage of the nose, organs and bronchiole and articular cartilage), elastic cartilage (for example, cartilage of the external ear, part of the Eustachian tube, and part of laryngeal cartilage), and fibrocartilage (for example, meniscus and endplate cartilage). The main purpose of cartilage is to provide a framework upon which bone deposition can begin and provide a smooth surface allowing free joint movement between bones. In addition, the cartilage provides a strong yet flexible support.

There are various therapies for treating a cartilage injury or cartilage failure. Osteoarthritis is degenerative arthritis that is, in general, relatively mild at first, but aggravates with time and wear. In terms of medical treatment, medicines such as an anti-inflammatory agent (for example, diclofenac, ibuprofen, or naproxen), a COX-2 selective inhibitor, hydrocortisone, glucosamine, and chondroitin sulfate are known to relieve pain due to cartilage loss.

Thrombospondin-2 (TSP-2) is a secretory, extracellular matrix glycoprotein that exhibits strong anti-angiogenic activity (Bornstein et al., 2000, Matrix Biology 19: 557-568).

Thrombospondin-1 (TSP-1) is a multimeric glycoprotein composed of identical monomers. The monomer has a molecular weight of about 185 KDa in sodium dodecyl sulfate polyacrylamide gel electrophoresis (SDS-PAGE) under reducing conditions. The predominant multimer is a trimer having a molecular weight of about 450 KDa on non-reducing gels, and the molecular weights by sedimentation equilibrium are similar, at 135 kDa for monomers and 420 kDa for trimers. The predicted molecular weight from a sequence of amino acid residues in the monomer is 127,524 Da, which does not include contributions from glycosylation and β-hydroxylation. TSP-1 is known to be involved in cell adhesion, proliferation, and chemotaxis. It has also been reported that TSP-1 may be involved in the progression of malignant tumors.

Interleukin-17B receptor (IL-17BR) is a protein in humans that is encoded by the IL17BR gene. IL-17BR is a cytokine receptor that specifically binds to IL17B and IL17E, but does not bind to IL17 and IL17O.

Heparin-binding epidermal growth factor-like growth factor (HB-EGF) exerts its biological activities by binding to an erb class of EGF receptors (EGFR). HB-EGF binds heparin with high affinity. HB-EGF binds to EGFR to modulate the biological effects of the growth factor on target cells, including cellular migration and proliferation. HB-EGF is mitogenic for fibroblasts, smooth muscle cells, and epithelial cells. HB-EGF is a heat-sensitive, cationic protein, with a molecular weight of approximately 22,000 Da. HB-EGF is known to treat symptoms associated with intestinal ischemia, for example, intestinal cell necrosis and enterocolitis. In addition, HB-EGF is known to inhibit liver diseases and liver cell death and facilitate liver reproduction in mammals.

In spite of these disclosures, association of chondrogenic differentiation of stem cells with TSP-1, TSP-2, IL-17BR, and HB-EGF has still not been proven.

SUMMARY OF THE INVENTION

One or more embodiments of the present invention provide thrombospondin 1 (TSP-1), TSP-2, interleukin 17B receptor (IL-17BR) and heparin-binding epidermal growth factor-like growth factor (HB-EGF) associated with stem cell activity or a stem cell expressing the same.

One or more embodiments of the present invention provide a method of using TSP-1, TSP-2, IL-17BR and HB-EGF associated with stem cell activity or a stem cell expressing the same.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above and other features and advantages of the present invention will become more apparent by describing in detail exemplary embodiments thereof with reference to the attached drawings in which.

DETAILED DESCRIPTION OF THE INVENTION

Figure 1:
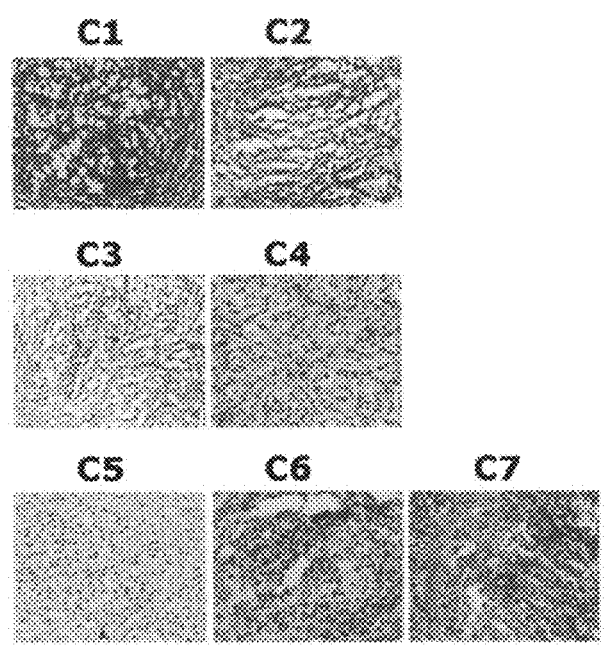
FIG. 1 illustrates images showing results of respectively differentiating 7 types of umbilical cord blood mesenchymal stem cell (UCB-MSC), i.e., C1, C2, C3, C4, C5, C6, and C7, cultured in differentiation media for 4 weeks, according to an embodiment of the present invention.

The present invention will now be described in detail with reference to the accompanying drawings.

According to an embodiment of the present invention, there is provided a composition for stimulating a cell to differentiate into a chondrocyte, the composition including at least one selected from the group consisting of thrombospondin 2 (TSP-2) and a cell expressing TSP-2.

TSP-2 is a secretory, extracellular matrix glycoprotein that exhibits strong anti-angiogenic activity (Bornstein et al., 2000, Matrix Biology 19: 557-568). TSP-2 is a disulfide-linked homotrimer glycoprotein, and, in humans, is encoded by the THBS2 gene. TSP-2 may have an amino acid sequence disclosed in RefSeq NP_003238 (human) (SEQ ID NO: 1) or NP_035711 (mouse) (SEQ ID NO: 2) or a sequence derived therefrom.

The composition may further include a carrier that may be pharmaceutically acceptable. For example, the carrier may be selected from the group consisting of a medium, a buffer, and a biocompatible polymer. The biocompatible polymer may be selected from commonly used polymers that may support cells and/or maintain cell activity in a two- or three-dimensional structure. For example, the biocompatible polymer may include at least one polymer selected from the group consisting of hyaluronic acid, hydroxy apatite, chitosan, collagen, and fibrin.

The composition may be used to treat or prevent injury, degeneration, loss or defect of cartilage. The injury, degeneration, loss or defect of cartilage may include arthritis or joint deformity. The arthritis may be rheumatic arthritis or degenerative arthritis. For example, the injury, degeneration, loss or defect of cartilage may be caused by at least one selected from the group consisting of degenerative arthritis due to aging; early degenerative arthritis due to joint overload, including obesity; external injuries due to sports, falling, accidents and the like; degenerative arthritis secondarily developed by not appropriately treating a cartilage injury due to external injuries; and joint deformity due to ligament injury, muscle weakness around joints, dislocation of joints, formation of joint mice and bone growth retardation. In addition, the cell to be differentiated into a chondrocyte may be a cell derived from at least one of tissues exposed by a cartilage injury, cartilage degeneration, cartilage loss, or a cartilage defect, for example, tissues such as synovial fluid, periosteum, bone, and bone marrow.

The composition may include TSP-2 in an amount ranging from about 30 µg to about 300 mg. For example, the composition may include TSP-2 in an amount ranging from about 10 ng to about 300 mg, from about 100 ng to about 300 mg, from about 1 µg to about 300 mg, from about 10 µg to about 300 mg, or from about 10 µg to about 300 mg.

In addition, the composition may include a cell producing TSP-2 in a concentration ranging from about $1\times10^4$ cells/ml to about $1\times10^6$ cells/ml, from about $5\times10^4$ cells/ml to about $1\times10^6$ cells/ml, from about $2.5\times10^5$ cells/ml to about $1\times10^6$ cells/ml, or from about $5\times10^5$ cells/ml to about $1\times10^6$ cells/ml.

The composition may facilitate the chondrogenic differentiation in vitro or in vivo. In the case of facilitation of the chondrogenic differentiation in vivo, a subject in which the chondrogenic differentiation occurs may be a mammal.

The cell may be a stem cell. The stem cell may be selected from the group consisting of an induced pluripotent stem cell (iPS cell), an embryonic stem cell, and an adult stem cell. The adult stem cell may be selected from the group consisting of a mesenchymal stem cell (MSC), an adipose-derived stem cell, an endothelial stem cell, and a hematopoietic stem cell. The MSC may be derived from a mammal, for example, a human. The MSC may include at least one selected from the group consisting of a bone marrow-derived mesenchymal stem cell (BM-MSC), an umbilical cord blood-derived mesenchymal stem cell (UCB-MSC), an adipose-derived mesenchymal stem cell (AD-MSC), an embryonic yolk sac-derived MSC, a placenta-derived MSC, a skin-derived MSC, a peripheral blood-derived MSC, a muscle-derived MSC, a liver-derived MSC, a nervous tissue-derived MSC, a periosteum-derived MSC, a umbilical cord-derived MSC, a fetal membrane-derived MSC, a synovium-derived MSC, an amniotic membrane-derived MSC, a meniscus-derived MSC, an anterior cruciate ligament-derived MSC, an articular chondrocytes-derived MSC, and an MSC separated and/or cultured from other tissues including MSCs.

The cell may be a cell that produces and extracellularly secretes the TSP-2. That is, the cell itself secretes TSP-2, and interacts with the TSP-2 to be differentiated into a chondrocyte. In addition, the cell may be a cell contacting TSP-2 that is produced by other cells to be secreted or externally administered. For example, the cell contacting TSP-2 may be a cell existing in tissue with a cartilage injury, cartilage degeneration, cartilage loss, or a cartilage defect. The cell existing in tissue with the cartilage injury, cartilage degeneration, cartilage loss, or cartilage defect may be a cell existing in tissue exposed due to the cartilage injury, cartilage degeneration, cartilage loss, or cartilage defect. The tissue exposed may vary depending on a degree of the cartilage injury, cartilage degeneration, cartilage loss, or cartilage defect. The tissue may be selected from the group consisting of synovial fluid, periosteum, bone, and bone marrow. The tissue may be a tissue with arthritis or joint deformity. The arthritis may be rheumatic arthritis or degenerative arthritis. The cell contacting TSP-2 may be a cell derived from at least one of the tissues with degenerative arthritis due to aging; early degenerative arthritis due to joint overload, including obesity; external injuries due to sports, falling, accidents and the like; degenerative arthritis secondarily developed by not appropriately treating a cartilage injury due to external injuries; and joint deformity due to ligament injury, muscle weakness around joints, dislocation of joints, formation of joint mice and bone growth retardation.

The "cell producing TSP-2" may be a cell that naturally produces TSP-2, or a cell induced to produce TSP-2. The composition may further include an inducer that induces a cell to produce TSP-2.

The cell producing TSP-2 may be a stem cell. The stem cell may be selected from the group consisting of an iPS cell, an embryonic stem cell, and an adult stem cell. The adult stem cell may be selected from the group consisting of an MSC, an adipose-derived stem cell, an endothelial stem cell, and a hematopoietic stem cell. The MSC may be derived from a mammal, for example, a human. The MSC may include at least one selected from the group consisting of a BM-MSC, an UCB-MSC, an AD-MSC, an embryonic yolk sac-derived MSC, a placenta-derived MSC, a skin-derived SMSC, a peripheral blood-derived MSC, a muscle-derived MSC, a liver-derived MSC, a nervous tissue-derived MSC, a periosteum-derived MSC, a umbilical cord-derived MSC, a fetal membrane-derived MSC, a synovium-derived MSC, an amniotic membrane-derived MSC, a meniscus-derived MSC, an anterior cruciate ligament-derived MSC, an articular chondrocytes-derived MSC, and an MSC separated and/or cultured from other tissues including MSCs.

The cell producing TSP-2 and the cell to differentiate into a chondrocyte may be identical or different from each other. That is, the cell producing TSP-2 may act by paracrine or autocrine mechanisms. The cell to differentiate into a chondrocyte may be a cell that produces TSP-2 and extracellularly secretes TSP-2. That is, the cell itself secretes TSP-2, and interacts with the secreted TSP-2, thereby differentiating into a chondrocyte. In addition, the cell may be a cell contacting TSP-2 that is produced by other cells to be secreted or externally administered. For example, the cell contacting TSP-2 may be a cell existing in tissue with a cartilage injury, cartilage degeneration, cartilage loss, or a cartilage defect. The cell existing in tissue with the cartilage injury, cartilage degeneration, cartilage loss, or cartilage defect may be a cell existing in the tissue itself and tissue exposed due to the cartilage injury, cartilage degeneration, cartilage loss, or cartilage defect. The tissue exposed may vary depending on a degree of the cartilage injury, cartilage degeneration, cartilage loss, or cartilage defect. For example, the tissue may be selected from the group consisting of synovial fluid, periosteum, bone, and bone marrow. The tissue may be a tissue with arthritis or joint deformity. The arthritis may be rheumatic arthritis or degenerative arthritis. The cell contacting TSP-2 may be a cell derived from at least one of the tissues with degenerative arthritis due to aging; early degenerative arthritis due to joint overload, including obesity; external injuries due to sports, falling, accidents and the like; degenerative arthritis secondarily developed by not appropriately treating a cartilage injury due to external injuries; and joint deformity due to ligament injury, muscle weakness around joints, dislocation of joints, formation of joint mice and bone growth retardation.

The cell producing TSP-2 may be a cell expressing TSP-2 to an amount higher than a set value. The set value may be an amount expressed by a reference cell. The reference cell may be known to have a chondrogenic differentiation capability. Such a differentiation capability may be known by the fact that the reference cell is cultured in an in vitro differentiation medium to induce chondorgenic differentiation. In addition, the reference cell administered to a subject may be identified to have a differentiation capability in vivo. The reference cell may be selected from the group consisting of a BM-MSC, a fibroblast, and an UCB-MSC. The UCB-MSC may be selected from the group consisting of a C5 UCB-MSC, a C6 UCB-MSC, and a C7 UCB-MSC.

The set value may be at least an amount expressed from an MSC that differentiates into a chondrocyte in a maintenance medium or an induction medium and has low activity. The MSC differentiating into a chondrocyte and with low activity may be a C5, C6 or C7 UCB-MSC.

The set value may be 72 pg/$10^5$ cells/ml or greater when the cell producing TSP-2 is cultured in a maintenance medium for 1 day. On the other hand, when the cell producing TSP-2 is pellet cultured in an induction medium for 7 days, the set value may be 550 pg/$10^5$ cells/ml or greater.

The set value may be a value of TSP-2 expressed in a medium selected from the group consisting of a α-minimum essential medium (MEM-α) medium, a MSC maintenance medium (for example, a MEM-α medium containing 10% fetal bovine serum (FBS) and 50 μg/ml of gentamicin), and a chondrogenic differentiation medium of a MSC (for example, a medium containing a high glucose Dulbecco's modified Eagle's medium (DMEM) (containing 4500 mg/l of glucose), 50 μg/ml of ascorbate, 0.1 μM dexamethasone, 40 μg/ml of L-proline, 100 μg/ml of pyruvate, 10 ng/ml of TGF-β3, 500 ng/ml of bone morphogenetic protein 6 (BMP-6), 1:100 concentration of ITS+ stock 16.25 μg/ml insulin, 6.25 μg/ml transferrin, 6.25 ng/ml selenious acid, 1.25 mg/ml BSA and 5.35 mg/ml linoleic acid, 1:100 dilution, Becton Dickinson), and 50 μg/ml of gentamicin).

The TSP-2 may be expressed in a cell lysate and/or a culture supernatant. The concentration of the TSP-2 may be measured on mRNA level or protein level.

The composition may stimulate activity of a cell to differentiate into a chondrocyte. The cell may be identical or different from the cell expressing TSP-2.

The cell may be a cell that produces TSP-2 and extracellularly secretes the TSP-2. That is, the cell itself secretes TSP-2, and interacts with the TSP-2 to be differentiated into a chondrocyte. In addition, the cell may be a cell contacting TSP-2 that is produced by other cells to be secreted or externally administered. For example, the cell contacting TSP-2 may be a cell existing in tissues with cartilage injury, cartilage degeneration, cartilage loss, or cartilage defect. The cell existing in tissue with a cartilage injury, cartilage degeneration, cartilage loss, or a cartilage defect may be a cell existing in the tissue itself or tissue exposed due to the cartilage injury, cartilage degeneration, cartilage loss, or cartilage defect. The tissue exposed may vary depending on a degree of the cartilage injury, cartilage degeneration, cartilage loss, or cartilage defect. The tissue may be selected from the group consisting of synovial fluid, periosteum, bone, and bone marrow. The tissue may be a tissue with arthritis or joint deformity. The arthritis may be rheumatic arthritis or degenerative arthritis. The cell contacting TSP-2 may be a cell derived from at least one of the tissues with degenerative arthritis due to aging; early degenerative arthritis due to joint overload including obesity; external injuries due to sports, falling, accidents and the like; degenerative arthritis secondarily developed by not appropriately treating a cartilage injury due to external injuries; and joint deformity due to ligament injury, muscle weakness around joints, dislocation of joints, formation of joint mice and bone growth retardation. For example, the cell may be located in the vicinity of the cell expressing TSP-2.

According to another embodiment of the present invention, there is provided a method of differentiating a cell into a chondrocyte in a subject, the method including administering a composition including at least one selected from the group consisting of TSP-2 and cells expressing TSP-2 to an amount effective enough to differentiate a cell into a chondrocyte.

The amount effective enough to differentiate a cell into a chondrocyte may be a sufficient amount at a constant ratio allowing chondrogenic differentiation of a cell. The amount may easily be selected by those of ordinary skill in the art according to the selected cell and a cell expressing TSP-2. For example, the amount may be an amount allowing at least 50%, at least 60%, at least 70%, at least 80%, or at least 90% of a total stem cell to differentiate into a chondrocyte within 1 to 7 days. A detailed description of the cell expressing TSP-2 and the cell to differentiate into a chondrocyte has already been provided. The subject may be selected from the group consisting of mammals, for example, a human, a mouse, and a rabbit.

According to another embodiment of the present invention, there is provided a method of identifying a capability of a stem cell to differentiate and/or induce a cell into a chondrocyte, the method including: culturing a stem cell in a medium; measuring the concentration of at least one selected from the group consisting of TSP-1, TSP-2, interleukin 17B receptor (IL-17BR), and heparin-binding epidermal growth factor-like growth factor (HB-EGF) from the culture; and identifying a chondrogenic differentiation and/or induction capability of the cultured stem cell based on the measured concentration.

The method will now be described in detail. The method includes culturing a stem cell in a medium. The culturing of the stem cell in a medium is known in the art, and thus media and conditions may be appropriately selected by one of ordinary skill in the art depending on selected stem cells.

The stem cell may be selected from the group consisting of an iPS cell, an embryonic stem cell, and an adult stem cell. The adult stem cell may be selected from the group consisting of an MSC, an adipose-derived stem cell, an endothelial stem cell, and a hematopoietic stem cell. The MSC may be derived from a mammal, for example, a human. The MSC may include at least one selected from the group consisting of a BM-MSC, an UCB-MSC, an adipose-derived MSC, an embryonic yolk sac-derived SMC, a placenta-derived MSC, a skin-derived MSC, a peripheral blood-derived MSC, a muscle-derived MSC, a liver-derived MSC, a nervous tissue-derived MSC, a periosteum-derived MSC, a umbilical cord-derived MSC, a fetal membrane-derived MSC, a synovium-derived MSC, an amniotic membrane-derived MSC, a meniscus-derived MSC, an anterior cruciate ligament-derived MSC, an articular chondrocytes-derived MSC, and an MSC separated and/or cultured from other tissues including MSCs.

For example, the stem cell may an MSC, and the medium may be an MSC maintenance medium or a chondrogenic differentiation medium of an MSC. The medium may be selected from the group consisting of a MEM-α medium, a MSC maintenance medium (for example, a MEM-a medium containing 10% FBS and 50 μg/ml of gentamicin), and a chondrogenic differentiation medium of an MSC (for example, a medium containing a high glucose DMEM, 50 μg/ml of ascorbate, 0.1 μM dexamethasone, 40 μg/ml of L-proline, 100 μg/ml of pyruvate, 10 ng/ml of TGF-β3, 500 ng/ml of BMP-6, 1:100 concentration of ITS+ stock (6.25 μg/ml insulin, 6.25 μg/ml transferrin, 6.25 ng/ml selenious acid, 1.25 mg/ml BSA and 5.35 mg/ml linoleic acid, 1:100 dilution, Becton Dickinson), and 50 μg/ml of gentamicin). The culturing process may be performed using a method that is commonly used in an MSC culture.

In the culturing of the stem cell in a medium, only the stem cell may be cultured without using other cells, or other cells, in addition to the stem cell may be cultured together. The other cells may be cells that produce TSP-2 and extracellularly secretes the TSP-2. That is, the cells themselves secrete TSP-2, and interact with the TSP-2, thereby differentiating into a chondrocyte. In addition, the cells may be cells contacting TSP-2 that is produced by other cells to be secreted or externally administered. For example, the cells contacting TSP-2 may be cells existing in tissues with cartilage injury, cartilage degeneration, cartilage loss, or cartilage defect. The cell existing in tissue with a cartilage injury, cartilage degeneration, cartilage loss, or a cartilage defect may be the tissue itself or a cell existing in tissue exposed due to the cartilage injury, cartilage degeneration, cartilage loss, or cartilage defect. The tissue exposed may vary depending on a degree of the cartilage injury, cartilage degeneration, cartilage loss, or cartilage defect. The tissue may be selected from the group consisting of synovial fluid, periosteum, bone, and bone marrow. The tissue may be a tissue with arthritis or joint deformity. The arthritis may be rheumatic arthritis or degenerative arthritis. The cell contacting TSP-2 may be a cell derived from at least one of the tissues with degenerative arthritis due to aging; early degenerative arthritis due to joint overload including obesity; external injuries due to sports, falling, accidents and the like; degenerative arthritis secondarily developed by not appropriately treating a cartilage injury due to external injuries; and joint deformity due to ligament injury, muscle weakness around joints, dislocation of joints, formation of joint mice and bone growth retardation. For example, the cell may be located in the vicinity of the cell expressing TSP-2.

The method includes measuring the concentration of at least one selected from the group consisting of TSP-1, TSP-2, IL-17BR, and HB-EGF from the culture. The concentration of at least one selected from the group consisting of TSP-1, TSP-2, IL-17BR, and HB-EGF may be measured from a cell lysate or a culture supernatant. The concentration of at least one selected from the group consisting of TSP-1, TSP-2, IL-17BR, and HB-EGF may be measured on an mRNA level or a protein level. The measurement on an mRNA or protein level is well-known in the art. For example, a quantitative polymerase chain reaction (PCR) or enzyme-linked immunosorbent assay (ELISA) may be used.

TSP-1 is a multimeric glycoprotein composed of identical monomers. The monomer has a molecular weight of about 185 kDa in sodium dodecyl sulfate polyacrylamide gel electrophoresis (SDS-PAGE) under reducing conditions. A predominant multimer is a trimer having a molecular weight of about 450 kDa on non-reducing gels, and molecular weights by sedimentation equilibrium are similar, at 135 kDa for monomers and 420 kDa for trimers. The predicted molecular weight from the sequence of amino acid residues in the monomer is 127,524 Da, which does not include contributions from glycosylation and β-hydroxylation. TSP-1 is known to be involved in cell adhesion, proliferation, and chemotaxis. It has also been reported that TSP-1 may be involved in the progression of malignant tumors. TSP-1 may have an amino acid sequence disclosed in RefSeq NP_003237 (human) (SEQ ID NO: 3) or NP_035710 (mouse) (SEQ ID NO: 4) or a sequence derived therefrom.

IL-17BR is a protein that in humans is encoded by the IL17RB gene. IL-17BR is a cytokine receptor that specifically binds to IL17B and IL17E, but does not bind to IL17 and IL17C. IL-17BR may have an amino acid sequence disclosed in RefSeq NP_758434 (human) (SEQ ID NO: 5) or NP_062529 (mouse) (SEQ ID NO: 6) or a sequence derived therefrom.

Heparin-binding epidermal growth factor-like growth factor (HB-EGF) exerts its biological activities by binding to an erb class of EGF receptors (EGFR). HB-EGF binds heparin with high affinity. HB-EGF binds to EGFR to modulate the biologic effects of the growth factor on target cells, including cellular migration and proliferation. HB-EGF may have an amino acid sequence disclosed in RefSeq NP_001936 (human) (SEQ ID NO: 7) or NP_034545 (mouse) (SEQ ID NO: 8) or a sequence derived therefrom.

The method may include identifying a chondrogenic differentiation and/or induction capability of the cultured stem cell based on the measured concentration.

The identifying process may include comparing the concentration of at least one selected from the group consisting of TSP-1, TSP-2, IL-17BR, and HB-EGF with the concentration obtained from a reference cell as a control, which is identified to have a chondrogenic differentiation capability.

In the identifying process, when the measured concentration is higher than the concentration obtained from the reference cell, it may be confirmed that the stem cell has a high capability of differentiating into a chondrocyte. On the other hand, when the measured concentration is lower than or the same as the concentration obtained from the reference cell, it may be determined that the stem cell has a low capability of differentiating into a chondrocyte.

The identifying process may include, when an expression amount of TSP-2 is larger than 72 pg/ml/$1.0 \times 10^5$ cells when the stem cell is monolayer cultured in a maintenance medium for 1 day, or when an expression amount of TSP-2 is larger than 550 pg/ml/$1.0 \times 10^5$ cells when the stem cell is pellet cultured in a maintenance medium for 7 days, determining that the stem cell has a high capability of differentiating into a chondrocyte. The maintenance medium of the stem cell may be a medium containing MEM-α, 10% FBS, and 50 μg/ml of gentamicin, and a chondrogenic induction medium of the stem cell may be a medium containing a high glucose DMEM, 50 μg/ml of ascorbate, 0.1 μM dexamethasone, 40 μg/ml of L-proline, 100 μg/ml of pyruvate, 10 ng/ml of TGF-β3, 500 ng/ml of BMP-6, 1:100 concentration of ITS+ stock (6.25 μg/ml insulin, 6.25 μg/ml transferrin, 6.25 ng/ml selenious acid, 1.25 mg/ml BSA and 5.35 mg/ml linoleic acid, 1:100 dilution, Becton Dickinson), and 50 μg/ml of gentamicin.

The method may further include comparing the measured concentration of at least one selected from the group consisting of TSP-1, TSP-2, IL-17BR, and HB-EGF with the concentration of at least one selected from the group consisting of TSP-1, TSP-2, IL-17BR, and HB-EGF obtained from a reference cell as a control, which is identified to have a low capability of differentiating into a chondrocyte.

In addition, in the comparing method, when the measured concentration of at least one selected from the group consisting of TSP-1, TSP-2, IL-17BR, and HB-EGF is at least 10%, at least 20% or at least 30% higher than the concentration of at least one selected from the group consisting of TSP-1, TSP-2, IL-17BR, and HB-EGF obtained from the reference cell, it may be determined that the stem cell has a high capability of differentiating into a chondrocyte. The reference cell may be selected from the group consisting of a BM-MSC, a fibroblast, and an UCB-MSC. The UCB-MSC may be selected from the group consisting of a C5 UCB-MSC, a C6 UCB-MSC, and a C7 UCB-MSC.

According to another embodiment of the present invention, there is provided a method of differentiating a cell into a chondrocyte, the method including differentiating a cell which is determined to have a high capability of differentiating into a chondrocyte according to the method described above, into a chondrocyte.

The differentiating process may be performed in vitro or in vivo. The method may include culturing a cell determined to have a high capability of differentiating into a chondrocyte, for example, an MSC, in a chondrogenic differentiation medium of a cell to differentiate the cell, for example, the MSC, into a chondrocyte in vitro. In the culturing process, the cell may be cultured with a biocompatible polymer.

The biocompatible polymer may be selected from commonly used polymers that may support cells and/or maintain cell activity in a two- or three-dimensional structure. For example, the biocompatible polymer may include at least one polymer selected from the group consisting of hyaluronic acid, hydroxyapatite, chitosan, fibrin, and collagen.

The method may further include administering the cell, for example, an MSC to a subject in need of chondrogenic differentiation. The subject may be a subject with cartilage injury, cartilage degeneration, cartilage loss, or cartilage defect. For example, the subject may be a subject with arthritis or joint deformity. The arthritis may be rheumatic arthritis or degenerative arthritis. The subject may have at least one of the tissues with degenerative arthritis due to aging; early degenerative arthritis due to joint overload including obesity; external injuries due to sports, falling, accidents and the like; degenerative arthritis secondarily developed by not appropriately treating a cartilage injury due to external injuries; and joint deformity due to ligament injury, muscle weakness around joints, dislocation of joints, formation of joint mice and bone growth retardation. The external injury includes a fracture. The administering process may be performed by intravenous injection or muscular injection, or may be locally performed on lesion sites. The cell, for example, a MSC may be administered with a carrier. The carrier may be a medium, a buffer, or a biocompatible polymer. The biocompatible polymer may be selected from commonly used polymers that may support cells and/or maintain cell activity in a two- or three-dimensional structure. The biocompatible polymer may include at least one polymer selected from the group consisting of hyaluronic acid, hydroxyapatite, chitosan, fibrin, and collagen. The cell may be a stem cell. The stem cell may include at least one selected from the group consisting of an iPS cell, an embryonic stem cell, and an adult stem cell. The adult stem cell may be selected from the group consisting of an MSC, an adipose-derived stem cell, an endothelial stem cell, and a hematopoietic stem cell. The MSC may be derived from a mammal, for example, a human. The MSC may include at least one selected from the group consisting of a BM-MSC, an UCB-MSC, an adipose-derived MSC, an embryonic yolk sac-derived MSC, a placenta-derived MSC, a skin-derived MSC, a peripheral blood-derived MSC, a muscle-derived MSC, a liver-derived MSC, a nervous tissue-derived MSC, a periosteum-derived MSC, a umbilical cord-derived MSC, a fetal membrane-derived MSC, a synovium-derived MSC, an amniotic membrane-derived MSC, a meniscus-derived MSC, an anterior cruciate ligament-derived MSC, an articular chondrocytes-derived MSC, and an MSC separated and/or cultured from other tissues including MSCs.

According to another embodiment of the present invention, there is provided a method of identifying a sample including a cell capable of differentiating into a chondrocyte, the method including culturing a cell-containing sample in a medium; and measuring the concentration of at least one selected from the group consisting of TSP-1, TSP-2, IL-17BR, and HB-EGF from the culture.

In the culturing process, the cell may be a stem cell. The stem cell may be a UCB-MSC. The cell capable of differentiating into a chondrocyte may be the stem cell, for example, the UCB-MSC. In addition, the cell capable of differentiating into a chondrocyte may be a stem cell, for example, a UCB-MSC and other cells cultured with the stem cell. The other cells may be other types of stem cells. The other cells may be cells that produce TSP-2 and extracellularly secretes the TSP-2. That is, the cells themselves secrete TSP-2, and interact with the TSP-2 to be differentiated into a chondrocyte. In addition, the cells may be cells contacting TSP-2 that is produced by other cells to be secreted or externally administered. For example, the cells contacting TSP-2 may be cells existing in tissues with a cartilage injury, cartilage degeneration, cartilage loss, or a cartilage defect. The cell existing in tissue with the cartilage injury, cartilage degeneration, cartilage loss, or cartilage defect may be a cell existing in the tissue itself and tissue exposed due to the cartilage injury, cartilage degeneration, cartilage loss, or cartilage defect. The tissue exposed may vary depending on a degree of the cartilage injury, cartilage degeneration, cartilage loss, or cartilage defect. For example, the tissue may be selected from the group consisting of synovial fluid, periosteum, bone, and bone marrow. The tissue may be a tissue with arthritis or joint deformity. The arthritis may be rheumatic arthritis or degenerative arthritis. The cell contacting TSP-2 may be a cell derived from at least one of the tissues with degenerative arthritis due to aging; early degenerative arthritis due to joint overload including obesity; external injuries due to sports, falling, accidents and the like; degenerative arthritis secondarily developed by not appropriately treating a cartilage injury due to external injuries; and joint deformity due to ligament injury, muscle weakness around joints, dislocation of joints, formation of joint mice and bone growth retardation. For example, the cell contacting TSP-2 may be a cell located in the vicinity of the cell expressing TSP-2. The medium may be a cell maintenance medium or a chondrogenic induction medium of a cell.

According to another embodiment of the present invention, there is provided a composition for decreasing chondrocyte death, the composition including a heparin binding EGF-like growth factor (HB-EGF) and a stem cell expressing a HB-EGF.

The HB-EGF may exert its biological activities by binding to an erb class of EGF receptors (EGFR). HB-EGF binds heparin with high affinity. HB-EGF binds to EGFR to modulate the biologic effects of the growth factor on target cells, including cellular migration and proliferation. HB-EGF may have an amino acid sequence disclosed in RefSeq NP_001936 (human) (SEQ ID NO: 7) or NP_034545 (mouse) (SEQ ID NO: 8) or a sequence derived therefrom.

The composition may include a stem cell expressing a HB-EGF. The stem cell may be an UCB-MSC. The composition may include a carrier. A detailed description of the carrier has already been provided.

According to another embodiment of the present invention, there is provided a method of decreasing chondrocyte death of a subject, the method including administering a composition for decreasing chondrocyte death to a subject, the composition including a HB-EGF in an amount enough to decrease chondrocyte death and a stem cell expressing a HB-EGF.

The amount enough to decrease chondrocyte death refers to an amount enough to decrease chondrocyte death more than a control. For example, the amount enough to decrease chondrocyte death refers to an amount enough to decrease chondrocyte death at least 10%, at least 20%, at least 30%, at least 40%, at least 50%, at least 60%, at least 70%, at least 80%, or at least 90% greater than a control. A detailed description of the composition has already been provided. The subject may be a subject with a cartilage injury, cartilage degeneration, cartilage loss, or a cartilage defect. The injury, degeneration, loss, or defect of cartilage may include arthritis, osteoporosis, a fracture, or joint deformity. The arthritis may be rheumatic arthritis or degenerative arthritis. The injury, degeneration, loss, or defect of cartilage may be derived from at least one selected from the group consisting of degenerative arthritis due to aging; early degenerative arthritis due to joint overload including obesity; external injuries due to sports, falling, accidents and the like; degenerative arthritis secondarily developed by not appropriately treating a cartilage injury due to external injuries; and joint deformity due to ligament injury, muscle weakness around joints, dislocation of joints, formation of joint mice and bone growth retardation. In addition, the chondrocyte may be a cell derived from at least one of the tissues exposed due to the injury, degeneration, loss, or defect of cartilage, for example, tissues such as synovial fluid, periosteum, bone, and bone marrow. The chondrocyte used herein includes a cell expressing cartilage specific extracellular matrix protein such as type II collagen and proteoglycan. The administering process may be performed by intravenous injection or muscular injection, or may be locally performed on lesion sites. The subject may be a mammal. The mammal may include a human, a cow, a pig, a dog, and a mouse.

The composition may further include a carrier. The carrier may be a medium, a buffer, or a biocompatible polymer. The biocompatible polymer may be selected from commonly used polymers that may support cells and/or maintain cell activity in a two- or three-dimensional structure. The biocompatible polymer may include at least one polymer selected from the group consisting of hyaluronic acid, hydroxyapatite, chitosan, fibrin, and collagen. The method may be performed in vitro or in vivo.

According to another embodiment of the present invention, there is provided a method of increasing an expression of at least one protein selected from the group consisting of TSP-1, TSP-2, IL-17BR, and HB-EGF from a stem cell, the method including culturing a stem cell in the presence of a joint fluid of a patient with at least one ailment selected from the group consisting of a cartilage injury, cartilage degeneration, cartilage loss, a cartilage defect, and combinations thereof.

The stem cell may be a BM-MSC or an UCB-MSC. The expression may be measured on a protein or mRNA level. The stem cell may be allogeneic or autologous with respect to the joint fluid.

The at least one ailment selected from the group consisting of the cartilage injury, cartilage degeneration, cartilage loss, cartilage defect, and combinations thereof may include arthritis and joint deformity. The arthritis may be rheumatic arthritis or degenerative arthritis. The ailment may include at least one selected from the group consisting of degenerative arthritis due to aging; early degenerative arthritis due to joint overload including obesity; external injuries due to sports, falling, accidents and the like; degenerative arthritis secondarily developed by not appropriately treating a cartilage injury due to external injuries; and joint deformity due to ligament injury, muscle weakness around joints, dislocation of joints, formation of joint mice and bone growth retardation. The method may be performed in vitro or in vivo. The joint fluid may be a cell existing in tissue itself with the ailment described above and in tissues exposed due to a cartilage injury, cartilage degeneration, cartilage loss, or a cartilage defect. The cell existing in tissue with the cartilage injury, cartilage degeneration, cartilage loss, or the cartilage defect may be a cell existing in the tissue itself and tissue exposed due to the cartilage injury, cartilage degeneration, cartilage loss, or cartilage defect. The tissue exposed may vary depending on a degree of the cartilage injury, cartilage degeneration, cartilage loss, or cartilage defect. For example, the tissue may be selected from the group consisting of synovial fluid, periosteum, bone, and bone marrow. In addition, the joint fluid may be a joint fluid located at an arbitrary position in a subject with the ailment.

According to another embodiment of the present invention, there is provided a method of differentiating a stem cell into a lesion tissue cell, the method including culturing a stem cell in the presence of a lesion tissue.

The lesion tissue may be a joint fluid of a patient with arthritis; a synovial fluid derived from a joint cavity of a patient with arthritis; a bronchoalveolar lavage fluid (BALF) of a patient with acute respiratory distress syndrome (ARDS), bronchial asthma, lung cancer, an interstitial lung disease, or a chronic obstructive pulmonary disease (COPD); or a spinal fluid, a pleural fluid, an ascetic fluid or a gastric fluid collected from a patient. The culturing process may be performed using a known method in the art related to culturing of stem cells.

The method may further include administering a stem cell differentiated into a lesion tissue cell, obtained by the culturing process, for example, a MSC, to a subject with a lesion tissue to treat the lesion tissue. The lesion tissue and the stem cell, for example, a MSC may be allogeneic or autologous with respect to each other.

In the method, the stem cell may include at least one selected from the group consisting of an iPS cell, an embryonic stem cell, and an adult stem cell. The adult stem cell may be selected from the group consisting of an MSC, an adipose-derived stem cell, an endothelial stem cell, and a hematopoietic stem cell. The MSC may be derived from a mammal, for example, a human. The MSC may include at least one selected from the group consisting of a BM-MSC, an UCB-MSC, an adipose-derived MSC, an embryonic yolk sac-derived MSC, a placenta-derived MSC, a skin-derived MSC, a peripheral blood-derived MSC, a muscle-derived MSC, a liver-derived MSC, a nervous tissue-derived MSC, a periosteum-derived MSC, an umbilical cord-derived MSC, a fetal membrane-derived MSC, a synovium-derived MSC, an amniotic membrane-derived MSC, a meniscus-derived MSC, an anterior cruciate ligament-derived MSC, an articular chondrocytes-derived MSC, and an MSC separated and/or cultured from other tissues including MSCs. The method may be performed in vitro or in vivo.

According to another aspect of the present invention, there is provided a method of screening a material regulating stem cell activity, the method including culturing a stem cell in the presence of a lesion tissue; and measuring a product expressed from the culture.

The method includes culturing a stem cell, for example, an MSC in the presence of a lesion tissue. The lesion tissue may be a joint fluid of a patient with arthritis; a synovial fluid derived from a joint cavity of a patient with arthritis; a bronchoalveolar lavage fluid (BALF) of a patient with acute respiratory distress syndrome (ARDS), bronchial asthma, lung cancer, an interstitial lung disease, or a chronic obstructive pulmonary disease (COPD); or a spinal fluid, a pleural fluid, an ascetic fluid or a gastric fluid collected from a patient. The culturing may be performed in the presence of a maintenance medium of the stem cell, for example, a MSC or a differentiation medium of the stem cell, for example, a MSC, into a tissue corresponding to a lesion tissue. The lesion tissue may be included in the culture in an amount ranging from 5 to 30%, for example, from 10 to 20% based on a cell suspension volume, a cell concentration, or a cell number. The culturing process may be performed using a known method in the art related to culturing of stem cells.

In the method, the stem cell may include at least one selected from the group consisting of an iPS cell, an embryonic stem cell, and an adult stem cell. The adult stem cell may be selected from the group consisting of an MSC, an adipose-derived stem cell, an endothelial stem cell, and a hematopoietic stem cell. The MSC may be derived from a mammal, for example, a human. The MSC may include at least one selected from the group consisting of a BM-MSC, an UCB-MSC, an adipose-derived MSC, an embryonic yolk sac-derived MSC, a placenta-derived MSC, a skin-derived MSC, a peripheral blood-derived MSC, a muscle-derived MSC, a liver-derived MSC, a nervous tissue-derived MSC, a periosteum-derived MSC, an umbilical cord-derived MSC, a fetal membrane-derived MSC, a synovium-derived MSC, an amniotic membrane-derived MSC, a meniscus-derived MSC, an anterior cruciate ligament-derived MSC, an articular chondrocytes-derived MSC, and an MSC separated and/or cultured from other tissues including MSCs. The method may be performed in vitro or in vivo.

The method includes measuring a product expressed from the culture. The measuring may be performed using a known method. For example, the measuring may be performed by quantitative PCR when the product is RNA. On the other hand, the measuring may be performed by ELISA when the product is protein. The product may be RNA or protein.

The method may include identifying a material regulating stem cell activity, for example, activity of an MSC, from the measured product. The activity of the stem cell, for example, the MSC, may be a differentiation activity. The method may further include comparing the amount of the measured product with the amount of a product obtained through a control experiment. The control experiment may be a negative or positive control experiment. The control experiment may be performed by culturing a stem cell, for example, an MSC, by not using a lesion tissue or in the presence of a normal tissue instead of a lesion tissue and measuring a product expressed from the culture.

The method may include, when the amount of the product is larger than that of the control, determining that the lesion tissue positively regulates the stem cell activity, for example, activity of the MSC. The method may include, when the amount of the product is smaller than that of the control, determining that the lesion tissue negatively regulates the stem cell activity, for example, activity of the MSC. The differentiation may be a differentiation into a tissue corresponding to a lesion tissue. For example, when the lesion tissue is a joint fluid, it may differentiate into a chondrocyte.

According to another embodiment of the present invention, there is provided a method of increasing an expression of at least one selected from the group consisting of TSP-2 and HB-EGF from a stem cell, the method including pellet culturing a stem cell.

The pellet culturing of the stem cell may be performed in a state where the stem cell is agglutinated tri-dimensionally. For example, the pellet culturing may be performed by centrifuging a cell-containing suspension to form a precipitated cell pellet and culturing the pellet. In this regard, an initial cell concentration used in the culturing may be $5 \times 10^5$ cells/ml to $5 \times 10^7$ cells/ml. The centrifuging process may be performed at 350 g to 1500 g for 5 to 30 minutes. The stem cell may be selected from the group consisting of an iPS cell, an embryonic stem cell, and an adult stem cell. The adult stem cell may be selected from the group consisting of an MSC, an adipose-derived stem cell, an endothelial stem cell, and a hematopoietic stem cell. The MSC may be derived from a mammal, for example, a human. The MSC may include at least one selected from the group consisting of a BM-MSC, an UCB-MSC, an adipose-derived MSC, an embryonic yolk sac-derived MSC, a placenta-derived MSC, a skin-derived MSC, a peripheral blood-derived MSC, a muscle-derived MSC, a liver-derived MSC, a nervous tissue-derived MSC, a periosteum-derived MSC, an umbilical cord-derived MSC, a fetal membrane-derived MSC, a synovium-derived MSC, an amniotic membrane-derived MSC, a meniscus-derived MSC, an anterior cruciate ligament-derived MSC, an articular chondrocytes-derived MSC, and an MSC separated and/or cultured from other tissues including MSCs.

The present invention will now be described more fully with reference to the following examples. These examples are for illustrative purposes only and are not intended to limit the scope of the present invention.

EXAMPLE 1

Identification of Secretory Proteins Specifically Induced in an UCB-MSC by Joint Fluid of Patient with Arthritis To identify a material regulating cartilage regeneration and cartilage inflammation produce by an UCB-MSC, a joint fluid of a patient with arthritis was added to a medium with an UCB-MSC being cultured therein to reach a final concentration of 20% (v/v), and then a resulting product was further cultured for 3 hours. The obtained culture supernatant was used as an analysis sample. In addition, as a control, an UCB-MSC culture cultured in a state where the joint fluid was not added thereto and/or a medium including 20% (v/v) joint fluid in which an UCB-MSC was not cultured were used. The joint fluid was obtained from a patient with degenerative arthritis.

Proteins expected to be included in each obtained culture or control sample were labeled with a detectable marker. The marker was biotin, and the biotin was detected by fluorescent detection of a complex formed by specific binding between the biotin and fluorescence-labeled streptavidin. Next, a protein chip with antibodies respectively binding to 507 secretory proteins immobilized thereon was treated with each sample (RayBiotech, Inc., RayBio™ Biotin Label-based Human Antibody Array I; Cat# AAH-BLG-1-2) to react together according to manufacturer guidelines. After the reaction, an excitation light of 532 nm was irradiated to the protein chip using a laser scanner (Axon Genepix Scanner 4000B) and a radiation light was detected at 635 nm. By comparing the obtained detection signal with a reference detection signal obtained from a control, the concentration of each protein in the sample was determined.

As a result of analysis, when the UCB-MSC was cultured in the presence of a joint fluid of a patient with arthritis, TSP-1, TSP-2, IL-17BR, and HB-EGF significantly increased, compared with the case where the UCB-MSC was cultured in the absence of a joint fluid of a patient with arthritis.

EXAMPLE 2

Association of Chondrogenic Differentiation of UCB-MSC with TSP-2

In the present example, association of the chondrogenic differentiation of an UCB-MSC with TSP-2 was evaluated. In addition, it was evaluated whether TSP-2 induced an UCB-MSC to differentiate into a chondrocyte.

1) Chondrogenic Differentiation Capability of Types of UCB-MSC

First, the chondrogenic differentiation capabilities of various types of UCB-MSC were confirmed. Each type of UCB-MSC was pellet cultured in a chondrogenic differentiation medium. The chondrogenic differentiation medium was a high glucose DMEM containing 50 µg/ml of ascorbate, 0.1 µM dexamethasone, 40 µg/ml of L-proline, 100 µg/ml of pyruvate, 10 ng/ml of TGF-β3, 500 ng/ml of BMP-6, 1:100 concentration of ITS+ stock (6.25 µg/ml insulin, 6.25 µg/ml transferrin, 6.25 ng/ml selenious acid, 1.25 mg/ml BSA and 5.35 mg/ml linoleic acid, 1:100 dilution, Becton Dickinson), and 50 µg/ml of gentamicin. An initial cell concentration was $5 \times 10^5$ cells/ml, and the culturing was performed in 15 ml polypropylene tube for 4 weeks. The medium was changed twice weekly, and a pellet was immobilized with 4% paraformaldehyde contained in paraffin, and cut to a piece with 5 µm thickness. The piece was stained with Safranin-O to detect an anionic proteoglycan.

FIG. 1 shows images of results of respectively differentiating 7 types of UCB-MSC, i.e., C1, C2, C3, C4, C5, C6, and C7 in a differentiation medium for 4 weeks, according to an embodiment of the present invention. Referring to FIG. 1, it is confirmed that C1 and C2, which may be classified to have good chondrogenic differentiation capabilities, each have cross-sections having round lacunae with distinct borders satisfactorily formed entirely thereon. In this regard, the lacunae are markers allowing confirmation of the presence of cartilage. In addition, C3 and C4, which may be classified to have medium chondrogenic differentiation capabilities, each have cross-sections having small lacunae with distinct borders entirely or partially formed thereon. In the cases of C5, C6, and C7, which may be classified to have poor chondrogenic differentiation capabilities, lacunae structures are barely formed. This indicates that the UCB-MSC has different differentiation capabilities due to genetic differences among individuals and differences in processes of collecting umbilical cord blood.

(2) Association of Chondrogenic Differentiation Capability with TSP-2

UCB-MSC types having different chondrogenic differentiation capabilities were each cultured in a chondrogenic differentiation medium for 1 week, and the amount of mRNA of TSP-2 was measured from the cultured cell by real time-PCR (RT-PCR) using a total RNA as a template and a TSP-2-specific primer.

Figure 2:
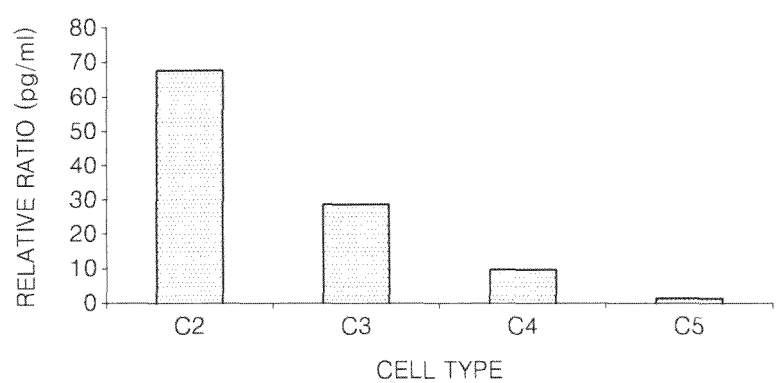
FIG. 2 is a graph showing an expression amount of mRNA of thrombospondin 2 (TSP-2) of an UCB-MSC cultured in a chondrogenic differentiation medium, according to an embodiment of the present invention.

FIG. 2 is a graph showing an expression amount of mRNA of TSP-2 of an UCB-MSC cultured in a chondrogenic differentiation medium, according to an embodiment of the present invention. Referring to FIG. 2, TSP-2 was expressed in the largest amount in a C1 (or C2) UCB-MSC having a high chondrogenic differentiation capability, while the expression of TSP-2 was weak in a C5 (C6 or C7) UCB-MSC having a low chondrogenic differentiation capability.

In addition, UCB-MSC types having chondrogenic differentiation capabilities were each cultured in a chondrogenic differentiation medium, and the concentration of TSP-2 in the obtained culture supernatant was analyzed by ELISA according to time.

Figure 3:
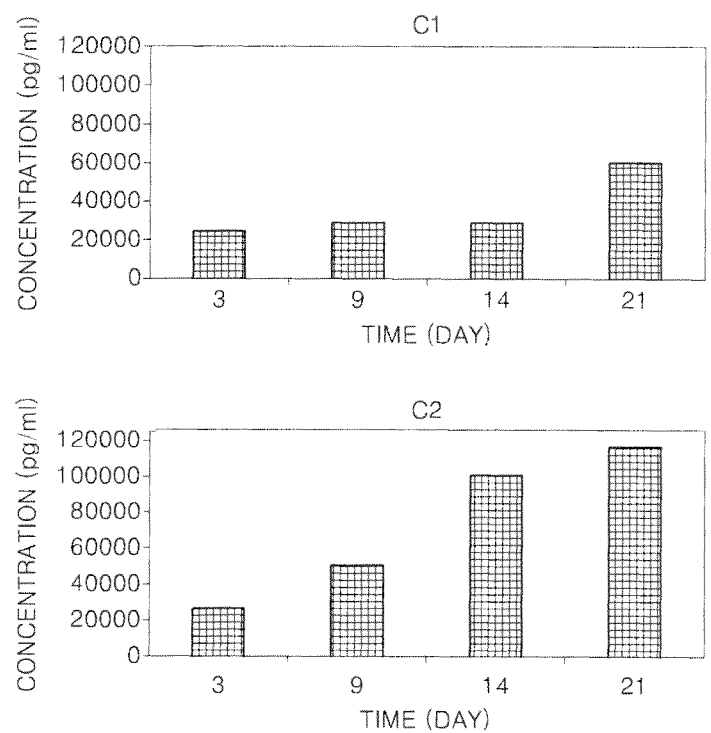
FIGS. 3 and 4 are graphs showing the amounts of TSP-2 in a culture supernatant, obtained by enzyme-linked immunosorbent assay (ELISA), according to embodiments of the present invention.
Figure 4:
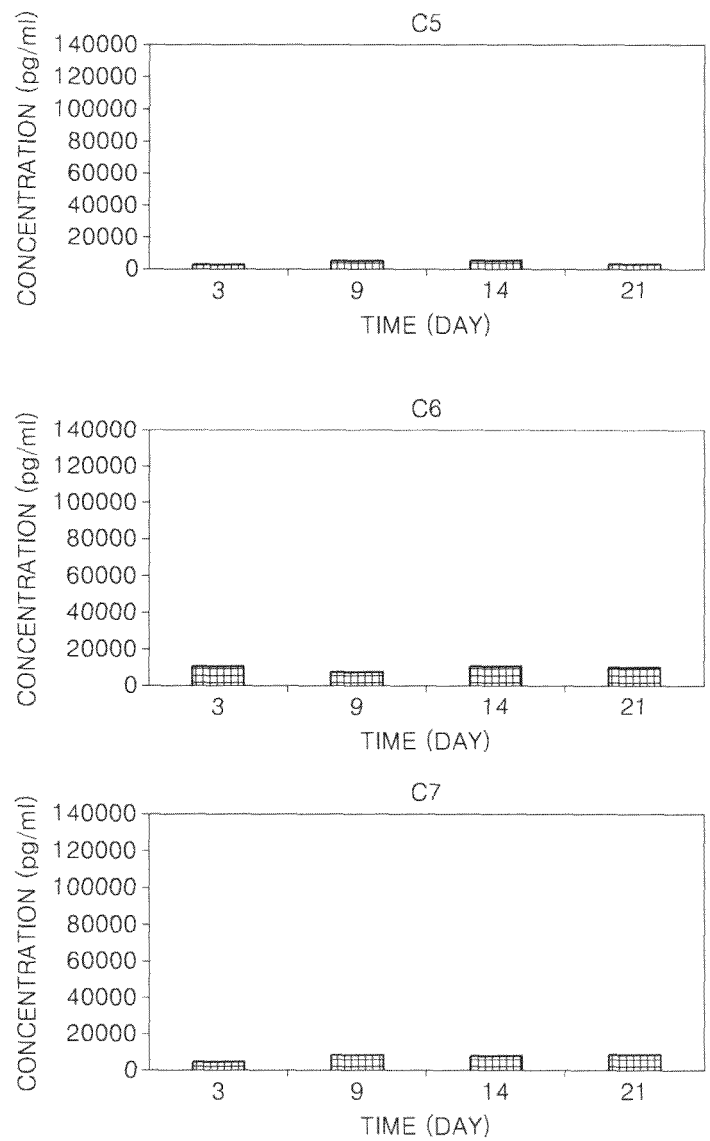

FIGS. 3 and 4 are graphs showing the amount of TSP-2 in a culture supernatant by ELISA, according to embodiments of the present invention. Referring to FIGS. 3 and 4, a high level of TSP-2 was expressed in a C1 or C2 UCB-MSC having a high chondrogenic differentiation capability (refer to FIG. 3), while a very low level of TSP-2 was expressed in a C5, C6, or C7 UCB-MSC (refer to FIG. 4).

(3) Activity of TSP-2 to Induce Chondrogenic Differentiation

An UCB-MSC was pellet cultured in a chondrogenic differentiation medium containing 10 ng/ml of isolated and purified human TSP-2 protein (R&D System, Minneapolis, Minn., USA), and a pellet size thereof was measured. As the UCB-MSC differentiates into a chondrocyte, the synthesis of extracellular matrix (ECM) increases, and thus the pellet size represents a degree of chondrogenic differentiation.

Figure 5:
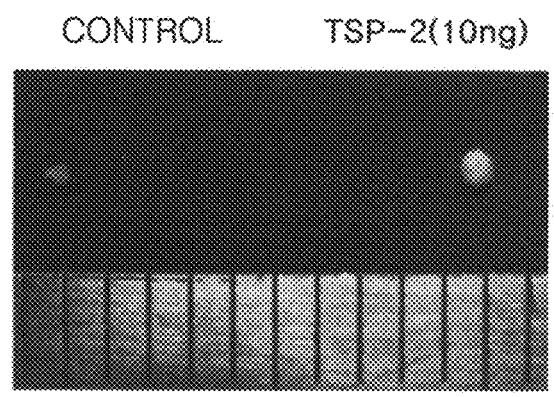
FIG. 5 illustrates an image showing a pellet size of an UCB-MSC cultured in the presence or absence of TSP-2, according to an embodiment of the present invention.

FIG. 5 is an image showing a pellet size of an UCB-MSC cultured in the presence or absence of TSP-2, according to an embodiment of the present invention. In FIG. 5, the pellet size of the control was 258526.070 $\mu m^2$, and, when the chondrogenic differentiation medium containing 10 ng/ml of TSP-2 was used, the pellet size was 3.49 times greater than that of the control, i.e., 901919.431 $\mu m^2$. As illustrated in FIG. 5, the pellet size of the UCB-MSC increased by TSP-2, which indicates that TSP-2 induces chondrogenic differentiation.

EXAMPLE 3

Expression Level of TSP-2 According to Chondrogenic Differentiation Capability

In the present example, an expression level of TSP-2 of an UCB-MSC according to its chondrogenic differentiation capability was measured. First, C3, C4 and C5 UCB-MSCs were each cultured in a chondrogenic differentiation medium under the same conditions for 7 days to induce chondrogenic differentiation. Relative chondrogenic differentiation capabilities of the C3, C4 and C5 UCB-MSCs were previously confirmed by an experiment, and satisfied the condition of C3>C4>C5. Next, TSP-2 in the obtained culture supernatant was measured by ELISA.

Figure 6:
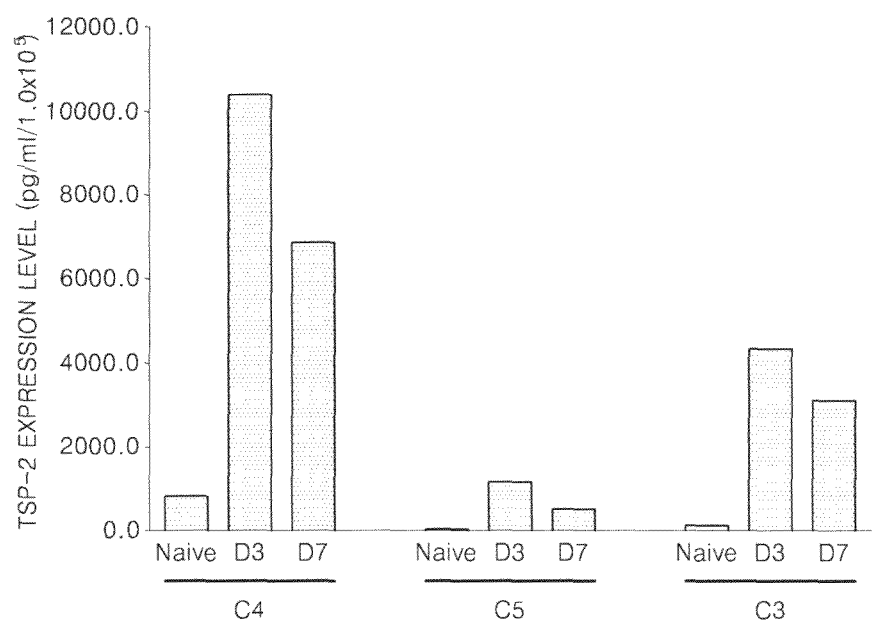
FIG. 6 is a graph showing TSP-2 expressed in a culture supernatant of each of 3 types of UCB-MSC cultured in a chondrogenic differentiation medium, according to an embodiment of the present invention.

FIG. 6 is a graph showing TSP-2 expressed in a culture supernatant of each of 3 types of UCB-MSC cultured in a chondrogenic differentiation medium, according to an embodiment of the present invention. Referring to FIG. 6, the C5 UCB-MSC, which was classified to have the lowest chondrogenic differentiation capability, secreted 72 pg/ml of TSP-2 per $1 \times 10^5$ cells in a state before chondrogenic differentiation induction (naive state), secreted 1.2 ng/ml of TSP-2 per $1 \times 10^5$ cells on the third day after chondrogenic differentiation induction, and secreted 0.550 ng/ml of TSP-2 per $1 \times 10^5$ cells on the seventh day after chondrogenic differentiation induction. Thus, an UCB-MSC expressing TSP-2 to a larger amount than that of TSP-2 expressed by the C5 UCB-MSC may be selected as an UCB-MSC suitable for use in chondrogenic differentiation.

EXAMPLE 4

Chondrogenesis Capabilities of UCB-MSC and BM-MSC

An in vitro chondrogenesis experiment was performed using a UCB-MSC and a BM-MSC each derived from about 10 different human donors.

(1) Preparation of UCB-MSC and BM-MSC

An umbilical cord blood (UCB) sample was obtained from the umbilical vein of deliveries under informed maternal consent. A bone marrow aspirate was obtained from an iliac crest of each donor under consent of each donor. Adherent and spindle-shaped mesenchymal stem cell (MSC)-like mononuclear cells were isolated from human BM and UCB through the same process. The following properties of the adherent and spindle-shaped MSC-like mononuclear cells obtained from the two origins were confirmed: (1) stemness (proliferativeness), (2) adhesion, (3) spindle shape, (4) cell surface antigens using flow cytometry, and capability to differentiate into mesenchymal tissue such as bone and cartilage.

A cell surface antigen phenotype of the adherent and spindle-shaped MSC-like mononuclear cells obtained from the two origins, confirmed to satisfy the requirements of (1) through (3), was negative for CD14, CD34 and CD45 (hemapoietic marker) and HLA-DR (class II marker), while it was positive for CD29, CD44, CD73, CD105 and CD90 (MSC marker) and HLA-ABC (class I marker). Since a fibroblast also expresses the same set of surface antigens as described above and is an adherent, spindle-shaped, proliferative cell, the properties of the MSC-like mononuclear cells were further confirmed to confirm appropriate differentiation potential of a MSC into mesenchymal tissue such as bone and cartilage.

(2) Confirmation of Chondrogenic Differentiation Capability and Property of Each Type of MSC A BM-MSC or a UCB-MSC was pellet cultured in a chondrogenic differentiation medium for 6 weeks to induce chondrogenesis. As the chondrogenic differentiation medium, a high glucose Dulbecco's modified Eagle Medium (DMEM) supplemented with 500 ng/ml bone morphogenetic protein-6 (BMP-6) (R&D System, Minneapolis, Minn., USA), 10 ng/ml transforming growth factor-β3 (TGFβ3) (Sigma), ITS+Premix (6.25 μg/ml insulin, 6.25 μg/ml transferrin, 6.25 ng/ml selenious acid, 1.25 mg/ml BSA, and 5.35 mg/ml linoleic acid, 1:100 dilution, Becton Dickinson), 100 nM dexamethasone (Sigma), 50 μg/ml of ascorbate-2-phosphate, 40 μg/ml of L-proline (Sigma), and 100 μg/ml of pyruvate (Sigma) was used. The chondrogenic differentiation medium is commonly used by one of ordinary skill in the art of chongrogenesis (see "Pellet Culture" in Materials and Methods of PNAS, Vol. 99, No. 7, pp. 4397-4402 (2002); "Chondrogenesis" in MATERIALS AND METHODS of Stem cells, 20 (2002): 530-41). It is known that the UCB-MSC and the BM-MSC easily differentiate into a chondrocyte.

An MSC at 4 to 6 passages was separated with trypsin, and then was suspended to $5 \times 10^5$/ml in the chondrogenic differentiation medium. Next, the suspension was added into a 15 ml polypropylene tube, and the MSC was centrifuged at 500 g for 5 minutes to form a pellet. The obtained pellet was cultured. The medium was changed twice weekly, and the pellet was immobilized with 4% paraformaldehyde contained in a paraffin according to time, and cut to a piece with 5 μm thickness. The piece was stained with Safranin-O to detect an anionic proteoglycan. In addition, the piece was subjected to type II collagen immunostaining. The chondrogenic differentiation was determined according to whether pellets having around shape were formed in a pellet culture, whether cartilage-specific proteoglycan existed in counter-staining by Safranin-O or Hematoxylin, and whether type II collagen existed in type II collagen immunostaining.

Figure 7:
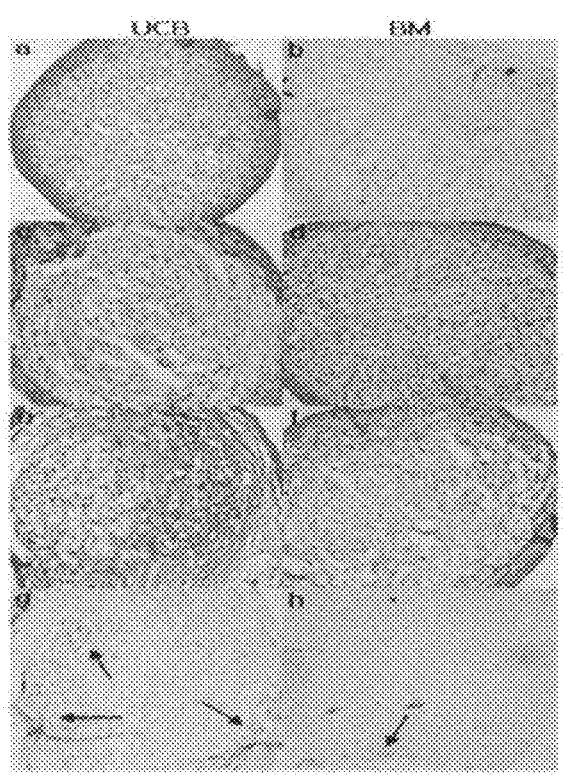
FIG. 7 illustrates images showing chondrogenic differentiation of an UCB-MSC and a bone marrow mesenchymal stem cell (BM-MSC) in vitro, according to an embodiment of the present invention.

FIG. 7 illustrates images showing in vitro chondrogenic differentiation of an UCB-MSC and a BM-MSC, according to an embodiment of the present invention. In FIG. 7, pellets a, c and e respectively represent Safranin-O staining results of the UCB-MSC obtained 1 week (a), 3 weeks (c), and 6 weeks (e) after in vitro chondrogenesis, and pellets b, d and f respectively represent Safranin-O staining results of the BM-MSC obtained 1 week (a), 3 weeks (c), and 6 weeks (e) after in vitro chondrogenesis. In addition, g and h respectively represent type II collagen immunostaining results of the UCB-MSC and the BM-MSC obtained 6 weeks after in vitro chondrogenesis.

Safranin-O-specific orange-red staining was more distinct in the UCB-MSC obtained 6 weeks after in vitro chondrogenesis than in the BM-MSC obtained 6 weeks after in vitro chondrogenesis (refer to e and f). In addition, collagen II immunostaining (indicated by arrows in FIG. 7) was more distinct in the UCB-MSC obtained 6 weeks after in vitro chondrogenesis than in the BM-MSC obtained 6 weeks after in vitro chondrogenesis (refer to g and h).

1 week after chondrogenesis induction, the UCB-MSC and the BM-MSC did not show distinct differences in the Safranin-O-specific orange-red staining. 3 weeks after chondrogenesis induction, the BM-MSC did not show any cartilage form, while the UCB-MSC began to exhibit a chondrocyte form. That is, in the case of the UCB-MSC, perichondrium-like cells were observed outside the pellet, an extra-cellular matrix began to be secreted inside the pellet, and the UCB-MSC began to be weakly positive for Safranin-O staining. 6 weeks after chondrogenesis induction, the BM-MSC showed the same chondrogenesis degree as that of the 3-week UCB-MSC, while the UCB-MSC showed a typical chondrogenesis tissue form. To confirm whether a functioning, normal chondrocyte is formed, collagen II immunostaining is performed, and as a result, brown-colored positive staining may be observed, as indicated by arrows in FIG. 7. Comparing the UCB-MSC with the BM-MSC, the UCB-MSC exhibits more positive than the BM-MSC, which indicates that the UCB-MSC has better chondrogenesis capability.

In conclusion, as illustrated in FIG. 7, the chondrogenesis capability of the UCB-MSC is significantly better than that of the BM-MSC.

Figure 8:
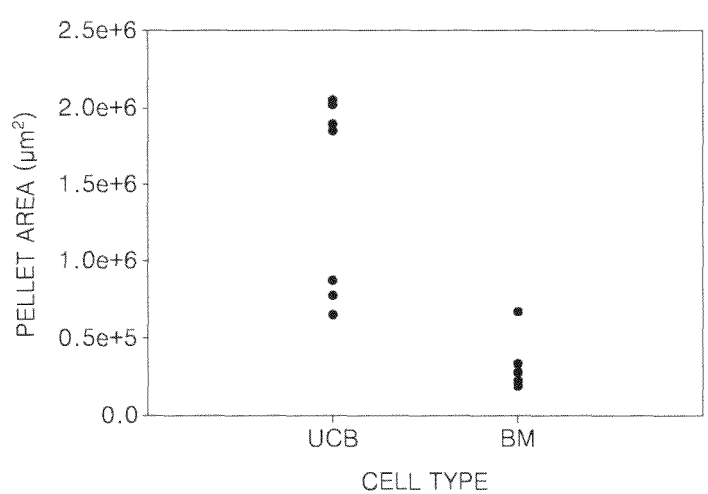
FIG. 8 is a graph showing capabilities of an UCB-MSC and a BM-MSC to differentiate into chondrogenic lineage, according to an embodiment of the present invention.

FIG. 8 is a graph showing capabilities of an UCB-MSC and a BM-MSC to differentiate into chondrogenic lineage, according to an embodiment of the present invention. An experiment for determining capabilities of the UCB-MSC and the BM-MSC to differentiate into the chondrogenic lineage was performed as follows. First, an MSC at 4 to 6 passages was separated with trypsin, and then was suspended to $5 \times 10^5$ cells/ml in a chondrogenic differentiation medium. Next, the suspension was added into a 15 ml polypropylene tube, and the MSC was centrifuged at 500 g for 5 minutes to form a pellet. The obtained pellet was cultured. The medium was changed twice weekly.

Referring to FIG. 8, 7 of 10 UCB-MSC samples (70%) had a capability to differentiate into the chondrogenic lineage, while 5 of 10 BM-MSC samples (50%) had a capability to differentiate into the chondrogenic lineage. 6 weeks after chondrogenic differentiation, the size of a pellet area of the UCB-MSC (n=7, $1450123.7 \pm 24256.9$ μm$^2$) (p<0.02) was much bigger than the size of a pellet area of the BM-MSC (n=5, $346531.3 \pm 87396.6$ μm$^2$). Pellet areas and areas positive for Safranin-O were measured by i-solution software (IM Technology, Doosan, Daejeon).

Figure 9:
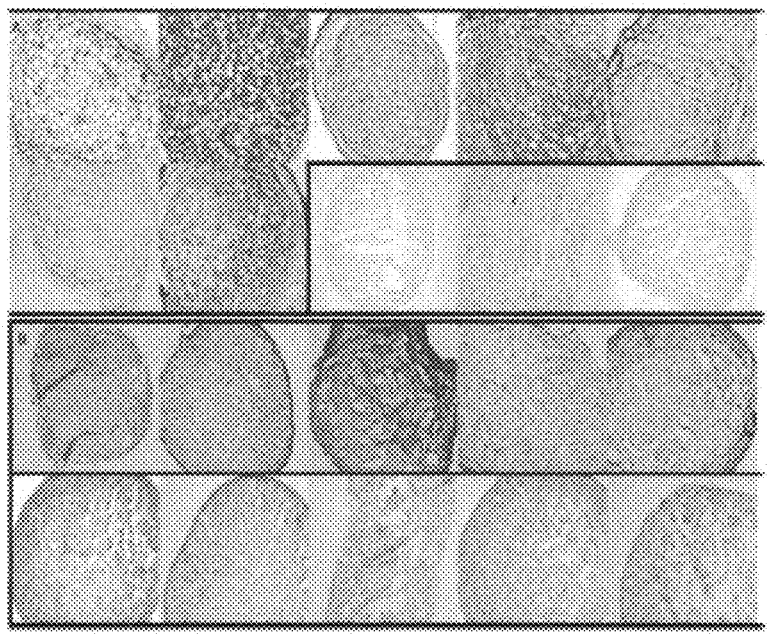
FIG. 9 illustrates images showing chondrogenic differentiation of 10 types of BM-MSC and 10 types of UCB-MSC analyzed on a sixth week after chondrogenic differentiation induction, according to an embodiment of the present invention.

FIG. 9 illustrates images showing chondrogenic differentiation of 10 types of BM-MSC and 10 types of UCB-MSC analyzed on the sixth week after chondrogenic differentiation induction, according to an embodiment of the present invention. Referring to FIG. 9, cartilage proteoglycan-specific orange-red staining by Safranin-O was distinct in 7 types of UCB-MSC (A panel-5 from an upper panel and 2 from a lower panel), while it was distinct in 5 types of BM-MSC (B panel-5 from the upper panel). That is, 70% of the total types of UCB-MSC differentiated into the chondrogenic lineage, while only 50% of the total types of BM-MSC differentiated into the chondrogenic lineage.

Figure 10:
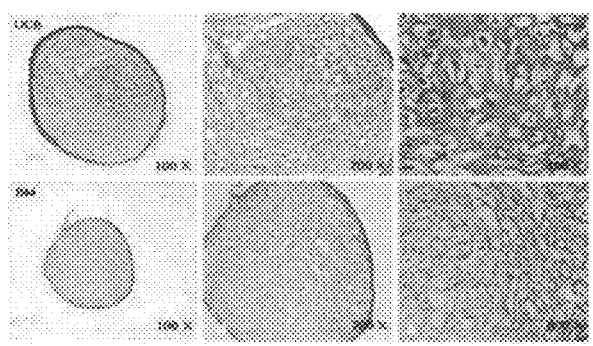
FIG. 10 illustrates images showing a difference in chondrogenesis capability between an UCB-MSC and a BM-MSC on the sixth week after chondrogenic differentiation induction, according to an embodiment of the present invention.

FIG. 10 illustrates images showing a difference in chondrogenesis capability between an UCB-MSC and a BM-MSC on the sixth week after chondrogenic differentiation induction, according to an embodiment of the present invention. FIG. 10 more clearly shows a difference between cartilage pellets produced from the UCB-MSC and cartilage pellets produced from the BM-MSC, wherein the same number of the UCB-MSC and the BM-MSC were cultured for 6 weeks under the same chondrogenic conditions. Referring to FIG. 10, the cartilage pellet produced from the UCB-MSC is obviously much bigger than the cartilage pellet produced from the BM-MSC. In addition, a cartilage-specific proteoglycan matrix was more abundant and distinct in the UCB-MSC-derived cartilage pellet with chondrocyte-like cells surrounding lacuna than in the BM-MSC-derived cartilage pellet. This indicates that the UCB-MSC has superior chondrogenesis capability to that of the BM-MSC under the same in vivo chondrogenic conditions.

Such results verify that the chondrogenic differentiation capability of the UCB-MSC is statistically significantly higher than the BM-MSC. Due to such a fact, MSCs may have significantly different differential cellular features, although MSCs are named the same. That is, this indicates that identical MSCs may also be classified as different cell types. In the present embodiment, a differentiation test was performed to test a difference in MSC cell types, wherein the differentiation depends on (1) the identity of MSCs different than terminally-differentiated fibroblasts and (2) in particular, the origin and age of a source tissue from which each type of MSC was isolated.

The same chondrogenic medium was used for the UCB-MSC and the BM-MSC. In addition, a growth factor combination contained in the medium is introduced for chondrogenesis of the BM-MSC and is well-known in the art (Biochemical and Biophysical Research Communications 320 (2004): Abstract on pp. 914-919, "Cell culture" and "Pellet culture" of Materials and Methods). Thus, specific medium conditions used in the present embodiment do not preferably affect the chondrogenic ability of the UCB-MSC. In conclusion, the UCB-MSC has superior in vitro chondrogenic activity to that of the BM-MSC.

EXAMPLE 5

Identification of Inducer of Expression of TSP-2 in UCB-MSC

In the present example, an inducer of expression of TSP-2 in a UCB-MSC was identified by varying culture conditions.

First, a UCB-MSC being monolayer cultured was treated with trypsin to be separated, and was suspended to a concentration of $5 \times 10^5$ cells/ml in a serum-free DMEM, and the resulting product was cultured for 24 hours. The medium used was a DMEM (containing 100 nM dexamethasone, 50 µg/ml of ascorbate-2-phosphate, 40 µg/ml of L-proline, and 100 µg/ml of pyruvate) and a DMEM supplemented with a growth factor selected from 10 ng/ml of TGF-β3 (Sigma), 500 ng/ml of BMP-6 (R&D System, Minneapolis, Minn., USA), and ITS+(6.25 µg/ml of insulin, 6.25 µg/ml of transferrin, 6.25 µg/ml of selenious acid, 1.25 mg/ml of BSA, and 5.35 mg/ml of linoleic acid, 1:100 dilution, Becton Dickinson). The UCB-MSC was monolayer cultured or pellet cultured. In the case of pellet culturing, the suspension was centrifuged at 500 g for 5 minutes to form a cell pellet, and the obtained cell pellet was cultured.

After the obtained culture supernatant was collected, a cell lysate was obtained, and a level of mRNA of TSP-2 of the UCB-MSC was measured by using a real-time polymerase chain reaction (RT-PCR) using a total RNA extracted from the cell lysate as a template.

Figure 11:
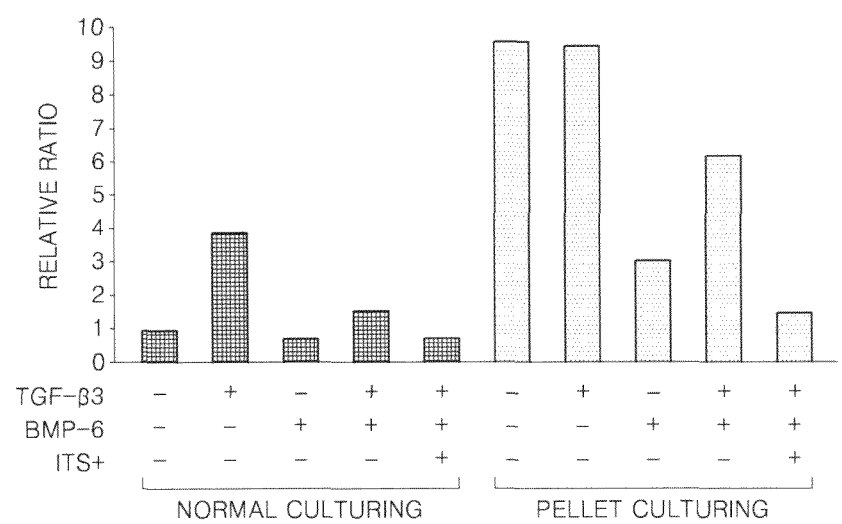
FIG. 11 is a graph showing expression results of TSP-2 under monolayer and pellet culturing conditions in the presence of a growth factor combination, according to an embodiment of the present invention.

FIG. 11 is a graph showing expression results of TSP-2 under monolayer and pellet culturing conditions in the presence of a growth factor combination, according to an embodiment of the present invention. Referring to FIG. 11, the expression of TSP-2 significantly increased under the pellet culturing conditions. In addition, from the results illustrated in FIG. 11, it was confirmed that the growth factor did not affect the expression of TSP-2.

EXAMPLE 6

Selection of Cell Types Suitable for Use in Chondrogenesis

A UCB-MSC was cultured in a medium that did not induce chondrogenesis, and it was confirmed whether an expression amount of TSP-2 was associated with a chondrogenic differentiation capability of the UCB-MSC.

In particular, C3 and C5 UCB-MSCs were monolayer cultured and pellet cultured in a serum-free DMEM (containing 100 nM dexamethasone, 50 µg/ml of ascorbate-2-phosphate, 40 µg/ml of L-proline, and 100 µg/ml of pyruvate) to a concentration of $5 \times 10^5$ cells/ml. The culturing conditions were the same as those in Example 5. The expression amount of TSP-2 in the obtained culture supernatant was measured by ELISA. In addition, the culturing conditions of a BM-MSC were also the same as those of the UCB-MSC.

Figure 12:
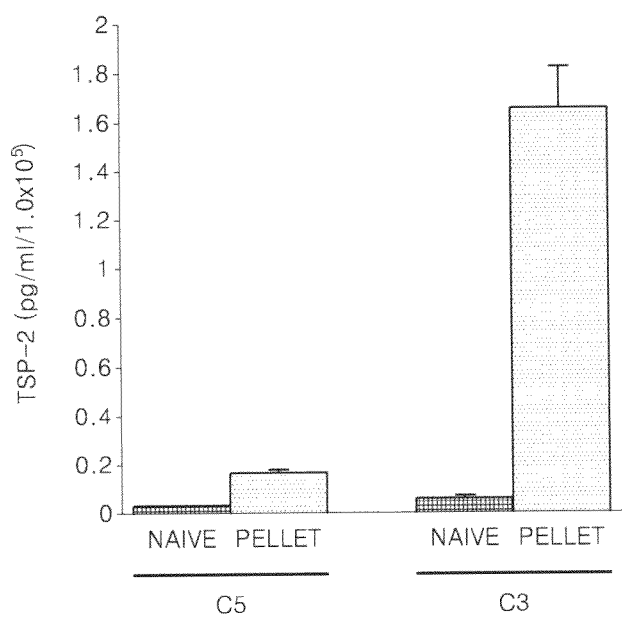
FIG. 12 is a graph showing an expression degree of TSP-2 according to the types of UCB-MSC, according to an embodiment of the present invention.

FIG. 12 is a graph showing an expression degree of TSP-2 according to the types of UCB-MSC, according to an embodiment of the present invention. In FIG. 12, C3 and C5 represent UCB-MSC cell types, and naive and pellet, respectively represent monolayer culturing for 24 hours and pellet culturing for 24 hours. Optical microscope observation results of C3 and C5 during the culturing process and after the culturing process are the same as those of C3 and C5 of FIG. 1.

Referring to FIG. 12, the monolayer cultured C5 (naive) expressed 33 to 72 pg/ml of TSP-2 per $1.0 \times 10^5$ cells, while the pellet cultured C5 (pellet) expressed 163 to 550 pg/ml of TSP-2 per $1.0 \times 10^5$ cells. It was previously confirmed that the chondrogenesis capability of the C3 UCB-MSC was better than that of the C5 UCB-MSC. Thus, whether a cell has a high chondrogenesis capability may be determined by comparing an expression amount of TSP-2 of the cell with an expression amount of TSP-2 of a reference cell, for example, a C5 UCB-MSC. For example, when a 1-day monolayer cultured (naive) reference cell expresses TSP-2 to an amount higher than 33 to 72 pg/ml per $1.0 \times 10^5$ cells, or when a 1-day pellet cultured reference cell expresses TSP-2 to an amount higher than 163 to 550 pg/ml per $1.0 \times 10^5$ cells, it may be determined that the chondrogenesis capability of the reference cell is higher than that of the C5 UCB-MSC. Such a method may be used to select MSCs suitable for use in chondrogenesis.

Based on the standard for selecting cells suitable for use in chondrogenesis, the reference cell may be appropriately selected by one of ordinary skill in the art.

As illustrated in FIG. 12, when a stem cell was pellet cultured, the expression of TSP-2 significantly increased.

Figure 13:
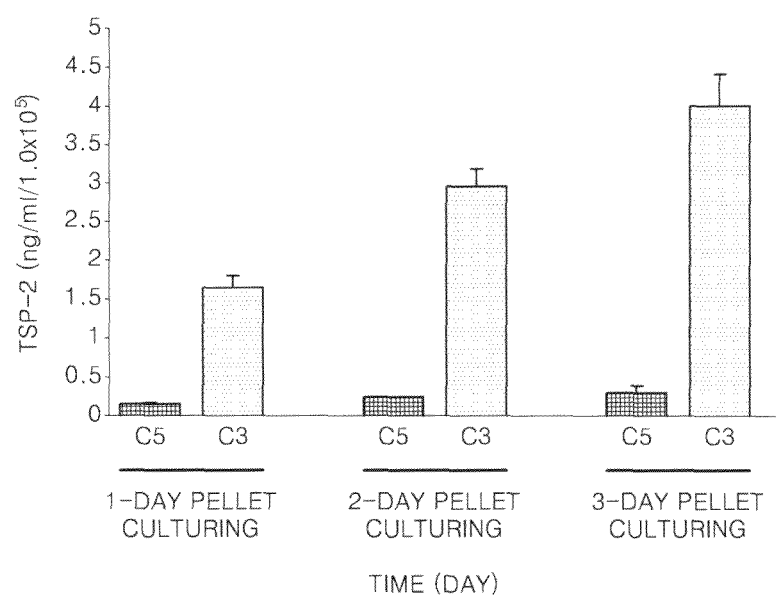
FIG. 13 is a graph showing measurement results of expression amounts of TSP-2 obtained by pellet culturing a C3 UCB-MSC and a C5 UCM-MSC for 3 days, according to an embodiment of the present invention.

FIG. 13 is a graph showing measurement results of expression amounts of TSP-2 obtained by pellet culturing a C3 UCB-MSC and a C5 UCB-MSC for 3 days, according to an embodiment of the present invention. Referring to FIG. 13, the expression amount of TSP-2 of the C5 UCB-MSC having a low chondrogenic differentiation capability was smaller than that of the C3 UCB-MSC having a high chondrogenic differentiation capability even as a culturing time increases.

Thus, the expression amount of TSP-2 is associated with the chondrogenic differentiation capability of the UCB-MSC, and the chondrogenic differentiation capability of MSCs may be predicted by measuring the expression amount of TSP-2.

Figure 26:
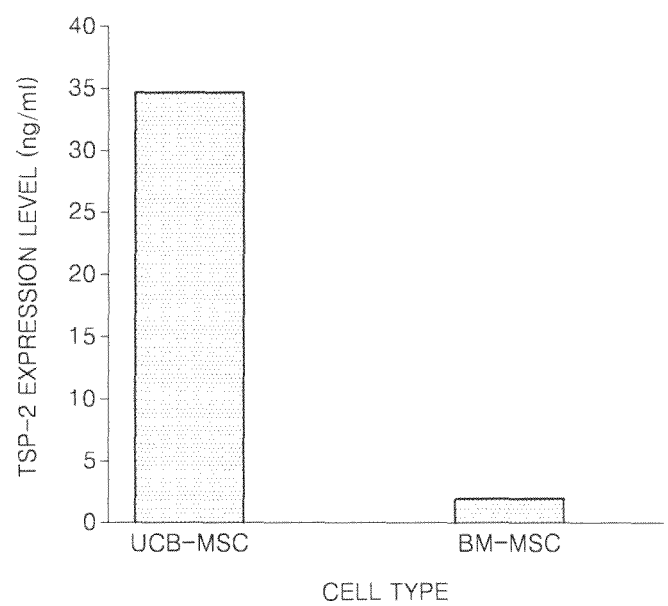
FIG. 26 is a graph showing results of pellet culturing an UCB-MSC and a BM-MSC, according to an embodiment of the present invention.

FIG. 26 is a graph showing results of measuring an expression level of TSP-2 after an UCB-MSC and a BM-MSC are pellet cultured, according to an embodiment of the present invention. Referring to FIG. 26, the UCB-MSC expressed a significantly higher level of TSP-2 than the BM-MSC. This indicates that the chondrogenic differentiation degree of the UCB-MSC is better than that of the BM-MSC.

The results illustrated in FIG. 26 were obtained as follows. First, an UCB-MSC and a BM-MSC that were being monolayer cultured were treated with trypsin to be separated, and the UCB-MSC and the BM-MSC were each suspended to a concentration of $5 \times 10^5$ cells/ml in a serum-free DMEM, and cultured for 24 hours. The medium used was a DMEM (containing 100 nM dexamethasone, 50 µg/ml of ascorbate-2-phosphate, 40 µg/ml of L-proline, and 100 µg/ml of pyruvate). Each cell was pellet cultured, and centrifuged at 500 g for 5 minutes to form a cell pellet, and the obtained cell pellet was cultured for 24 hours. The obtained culture supernatant was collected, and the expression level of TSP-2 was measured by ELISA.

EXAMPLE 7

Expression of TSP-2 by UCB-MSC Under Chondrogenic Differentiation and Dedifferentiation Conditions To confirm association of an expression amount of TSP-2 with chondrogenic differentiation, the expression amount of TSP-2 by an UCB-MSC was measured under chondrogenic differentiation and dedifferentiation conditions.

(1) Expression of TSP-2 by Mesenchymal Cell Under Chondrogenic Differentiation Condition A mesenchymal cell (also called chondrogenic progenitor cell) was separated from a limb bud of a mouse embryo. $4 \times 10^7$ cells/ml of the separated mesenchymal cell was resuspended in a medium (containing DMEM/F-12 (2:3), 10% (v/v) FBS, 50 µg/ml of streptomycin, and 50 units/ml of penicillin), and each of 15 µl of the resuspended mesenchymal cell was dropped into a culture dish to be attached thereto in an independent spot form. Next, the mesenchymal cell in a spot form was cultured for 6 days to induce each spot to differentiate into a chondrocyte. An expression amount of TSP-2 was measured by using RT-PCR using a total RNA isolated from the cell as a template.

Figure 14:
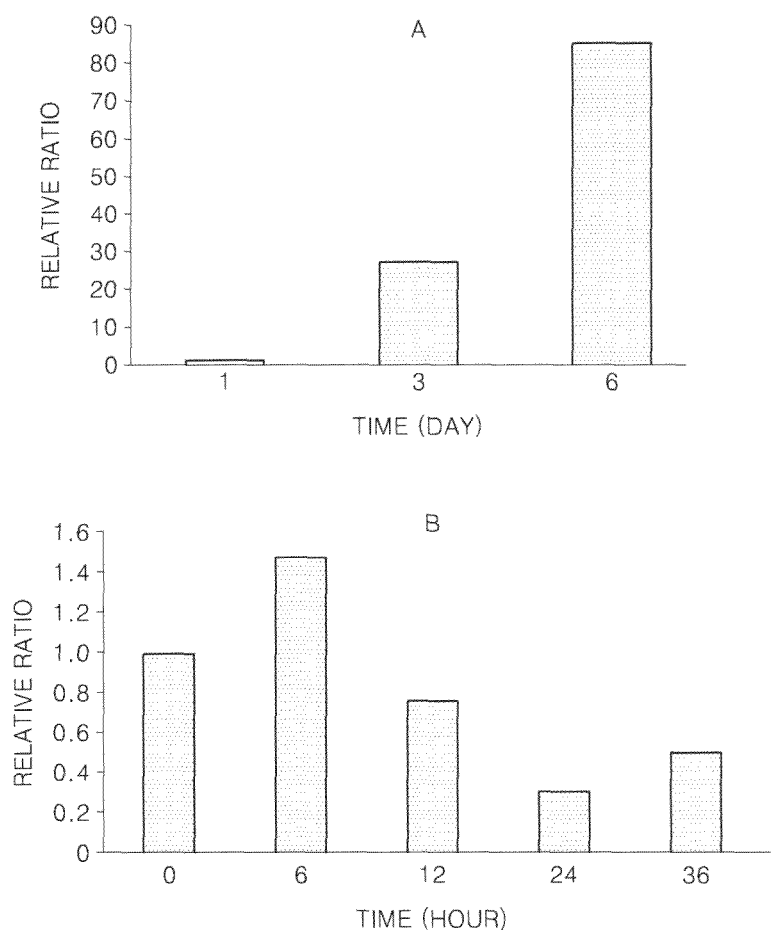
FIG. 14 illustrates graphs showing the amount of TSP-2 expressed by an UCB-MSC under differentiation and dedifferentiation conditions, according to an embodiment of the present invention.

FIG. 14 illustrates graphs showing the amount of TSP-2 expressed by a mesenchymal cell or a chondrocyte under differentiation and dedifferentiation conditions, according to an embodiment of the present invention. Referring to A of FIG. 14, the expression amount of TSP-2 increased with a culturing time under differentiation conditions.

(2) Expression of TSP-2 by Chondrocyte Under Chondrogenic Dedifferentiation Condition A chondrocyte was separated from a knee joint of a 2-week-old rabbit. The separated chondrocyte was cultured in a medium containing a DMEM, 10% (v/v) FBS, and 50 µg/ml of gentamicin in the presence of 5 ng/ml of interleukin-1β(IL-1β) to induce dedifferentiation. IL-1β is a pro-inflammatory cytokine that dedifferentiates a chondrocyte, resulting in loss of the properties of the chondrocyte. The expression amount of TSP-2 was measured by RT-PCR using a total RNA isolated from the cell as a template.

Referring to B of FIG. 14, the expression amount of TSP-2 decreased with a culturing time under dedifferentiation conditions.

From the results described above, it is confirmed that the expression of TSP-2 is associated with chondrogenic differentiation and dedifferentiation of a chondrocyte.

EXAMPLE 8

Chondrogenic Differentiation Induction of UCB-MSC by TSP-2

An UCB-MSC was cultured in the presence of TSP-2 to induce chondrogenic differentiation. The medium used was the chondrogenic culture medium described above. A recombinant TSP-2 (R&D System, Minneapolis, Minn., USA) was added to the medium in an amount of 10 ng/ml to 500 ng/ml, and the resultant was pellet cultured. An initial concentration of the UCB-MSC was $5 \times 10^5$ cells/ml. After the culturing process, a RT-PCR using a total RNA isolated from the cell as a template and using primers specific to a chondrocyte marker (for example, type II collagen (Col IIA1), aggrecan (Acan), Sox-9 and TSP-2); and hypertrophic chondrocyte and bone markers (for example, Col IA1 and Col XA1) was performed to measure an expression amount of mRNA of these markers.

Figure 15:
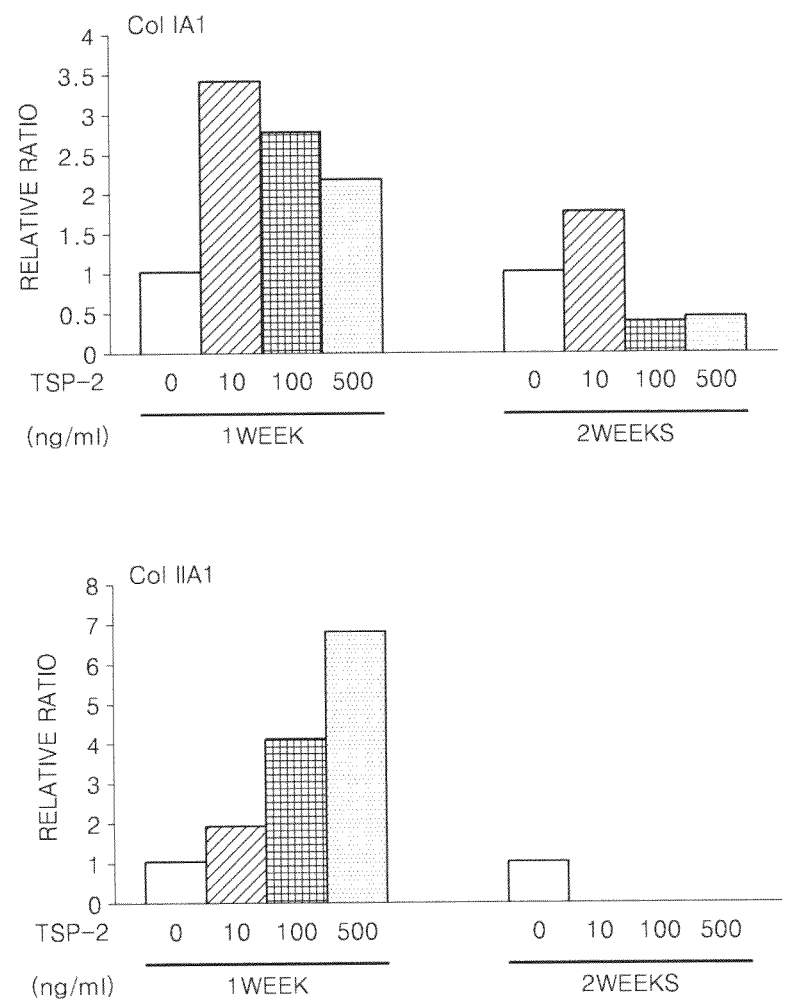
FIGS. 15 through 17 are graphs showing an expression amount of a marker protein of an UCB-MSC cultured in the presence of TSP-2, according to embodiments of the present invention.
Figure 16:
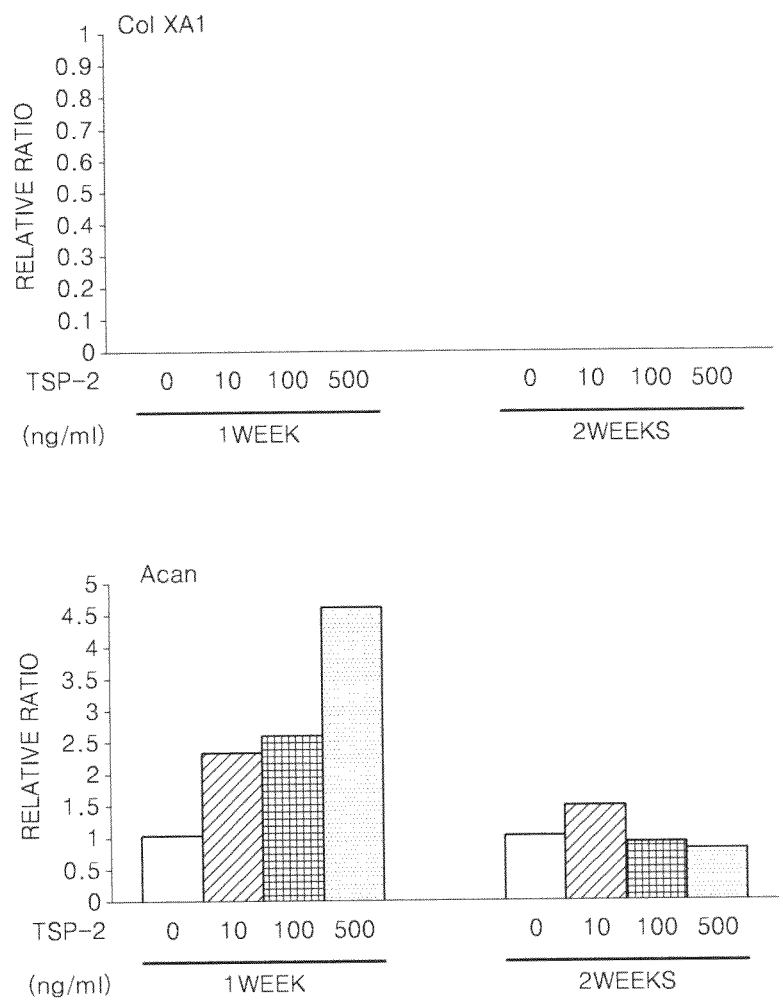
Figure 17:
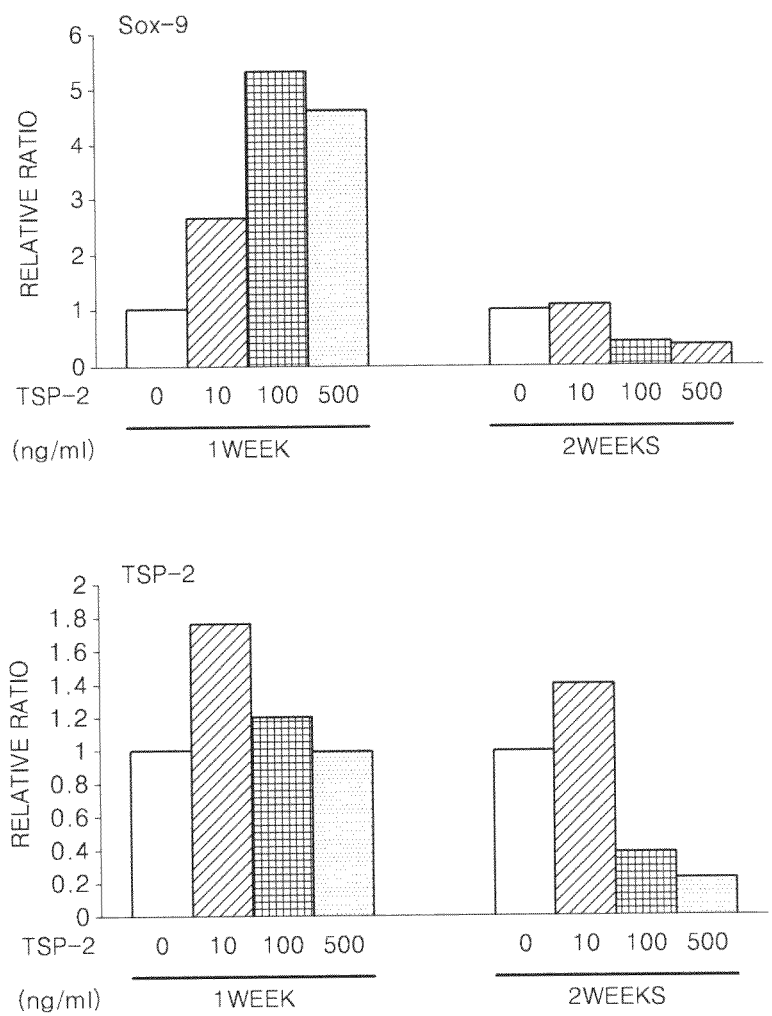

FIGS. 15 through 17 are graphs showing an expression amount of a marker protein of an UCB-MSC cultured in the presence of TSP-2, according to embodiments of the present invention. Referring to FIGS. 15 through 17, the expressions of type II collagen (Col IIA1), aggrecan (Acan), and Sox-9 increased depending on the concentration thereof 1 week after the chondrogenic differentiation induction, while the expressions of Col 1A1 and Col XA1 decreased or were not exhibited with a culturing time.

Thus, it is confirmed that externally added TSP-2 stimulates chondrogenic differentiation of the UCB-MSC.

EXAMPLE 9

Chondrogenic Differentiation Induction of UCB-MSC Under TSP-2 Expression-Inhibiting Conditions An UCB-MSC was cultured in a chondrogenic culture medium under TSP-2 expression-inhibiting conditions to induce chondrogenic differentiation.

Small interfering RNA (siRNA) (Bioneer, Daejeon, Korea, sense sequence: SEQ ID NO:9, anti-sense sequence: SEQ ID NO: 10) with a sequence complementary to that of mRNA of TSP-2 was added to a medium in a concentration of 33 nM to inhibit the expression of TSP-2. The medium used was the chondrogenic culture medium described above, and the UCB-MSC was pellet cultured. An initial concentration of the UCB-MSC was $5 \times 10^5$ cells/ml, and the culturing process was performed for 7 days. The expression amount of TSP-2 was measured by using RT-PCR using a total RNA extracted from the UCB-MSC and using a TSP-2-specific primer, or the expression amount of TSP-2 in the obtained culture supernatant was measured by ELISA. The expressions of Col IIA1 and aggrecan were measured by using a RT-PCR.

Figure 18:
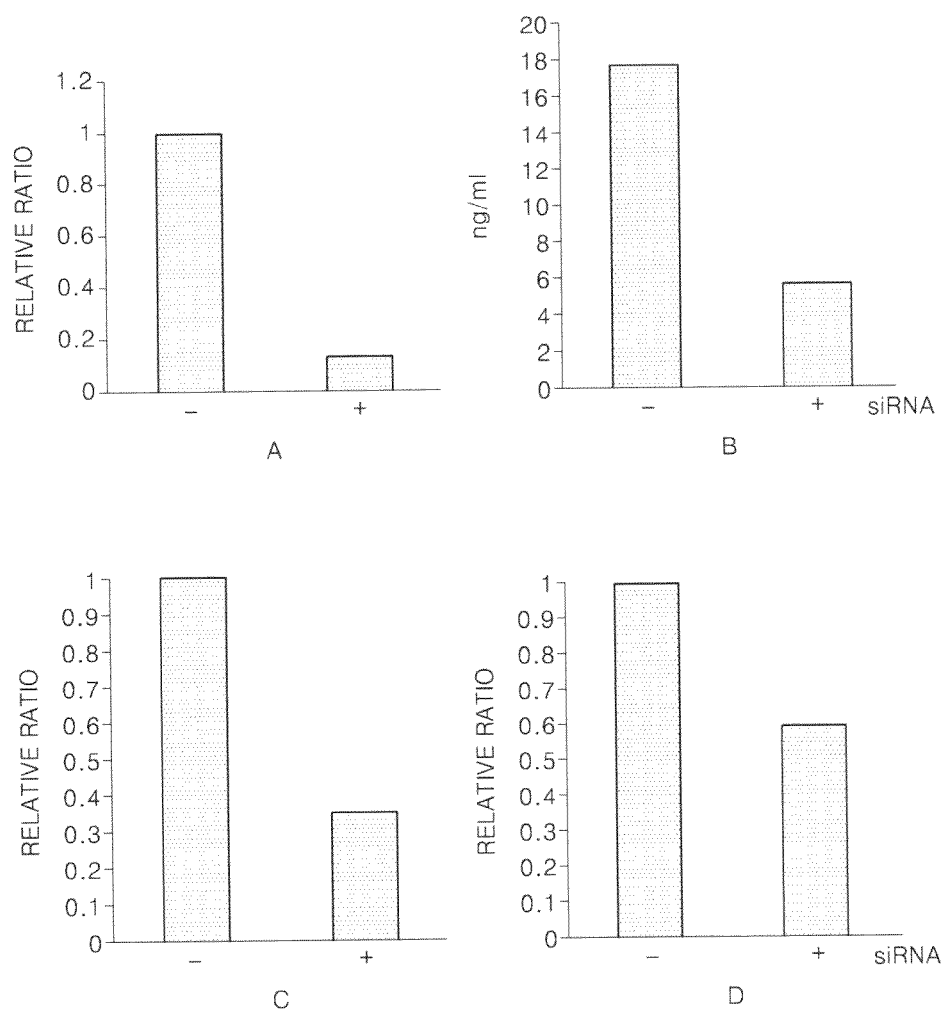
FIG. 18 illustrates graphs showing a degree of chondrogenic differentiation of an UCB-MSC cultured in a chondrogenic medium under TSP-2 expression-inhibiting conditions, according to an embodiment of the present invention

FIG. 18 illustrates graphs showing a degree of chondrogenic differentiation of an UCB-MSC cultured in a chondrogenic medium under TSP-2 expression-inhibiting conditions, according to an embodiment of the present invention. Referring to FIG. 18, in the UCB-MSC cultured under TSP-2 expression-inhibiting conditions, i.e., in the presence of siRNA of TSP-2, the expressions of the chondrocyte markers, i.e., Col IIA1 and aggrecan significantly decreased. This indicates that TSP-2 induces or stimulates the chondrogenic differentiation of the UCB-MSC. In FIG. 18, A shows results of measuring the concentration of TSP-2 by RT-PCR, B shows results of measuring the concentration of TSP-2 by ELISA, and C and D show RT-PCR results of Col IIA1 and aggrecan, respectively.

EXAMPLE 10

Level of TSP-2 in Blood Plasma of Patient with Osteoarthritis

Blood was collected from 15 normal people and 28 patients with osteoarthritis, and the level of TSP-2 in each blood plasma was measured by ELISA.

Figure 19:
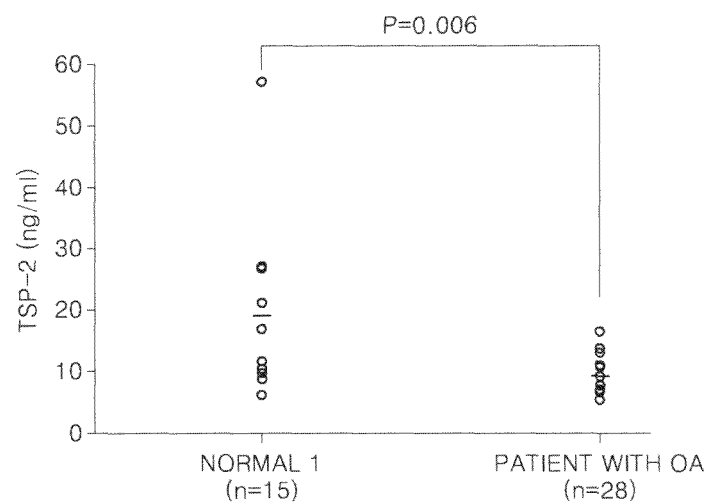
FIG. 19 is a graph showing a level of TSP-2 in blood plasma of a normal person and a patient with osteoarthritis, according to an embodiment of the present invention.

FIG. 19 is a graph showing levels of TSP-2 in blood plasma of a normal person and a patient with osteoarthritis, according to an embodiment of the present invention. Referring to FIG. 19, the level of TSP-2 was lower in the blood plasma of the patient with osteoarthritis than in the blood plasma of the normal people. This indicates that the level of TSP-2 in blood may act as a marker for diagnosing arthritis. This also indicates that the level of TSP-2 in blood may act as a marker for diagnosing chondrogenic differentiation-related diseases, in addition to arthritis.

EXAMPLE 11

Expression of TSP-1 in UCB-MSC by Joint Fluid of Patient with Arthritis

The effect of a joint fluid of a patient with arthritis on the expression of TSP-1 in an UCB-MSC was confirmed.

An UCB-MSC was cultured in the presence of a joint fluid of a patient with arthritis. The UCB-MSC was cultured in a medium containing MEM-α, 10% (v/v) FBS, and 50 μg/ml of gentamicin for 5 to 6 days. The joint fluid of joint cavity was added to the medium when the UCB-MSC was cultured to a level of 70-80% of the area of a culture container. The joint fluid of the patient with arthritis was added to a concentration of 20% (v/v) after the medium with the UCB-MSC being cultured therein was changed to a medium containing MEM-α and 50 μg/ml of gentamicin, and the resultant was further cultured for 3 hours. The obtained culture was used as an analysis sample. In addition, as a control, an UCB-MSC culture cultured in a state where the joint fluid was not added thereto and/or a medium with the joint fluid added to a concentration of 20% (v/v) in which an UCB-MSC was not cultured were used. The joint fluid was obtained from a patient with degenerative arthritis.

Figure 20:
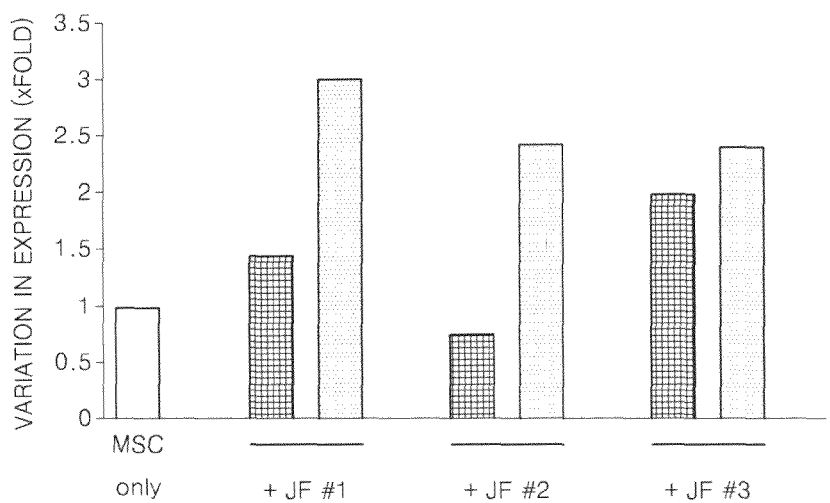
FIGS. 20 and 21 are graphs showing expression amounts of TSP-1 of an UCB-MSC in the presence of a joint fluid of a patient with arthritis, according to embodiments of the present invention.
Figure 21:
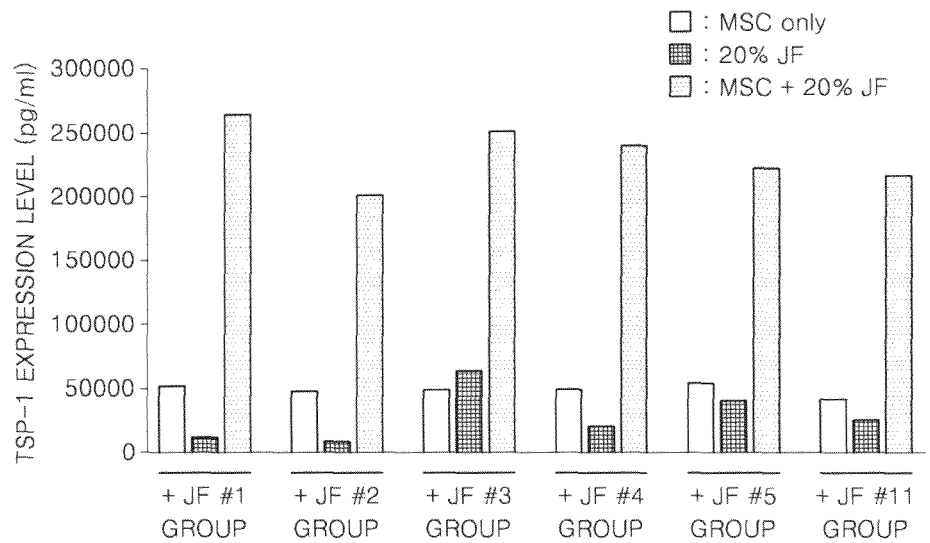

FIGS. 20 and 21 are graphs showing expression amounts of TSP-1 of an UCB-MSC in the presence of a joint fluid of a patient with arthritis, according to embodiments of the present invention. In FIG. 20, MSC only represents that the UCB-MSC was cultured without the joint fluid, and JF#1, JF#2, and JF#3 respectively represent joint fluids of different patients, and results from a triplicate experiment. In FIG. 20, the expression amount of TSP-1 was measured by using a RT-PCR using a total RNA extracted from the UCB-MSC as a template and using a TSP-1-specific primer.

In FIG. 21, JF represents a joint fluid of a patient with arthritis. In FIG. 21, the expression amount of TSP-1 in the obtained culture supernatant of the UCB-MSC was measured by ELISA. Referring to FIG. 21, the UCB-MSC cultured in the presence of a joint fluid of a patient with arthritis expressed a larger amount of TSP-1 than that in the UCB-MSC cultured in a medium excluding the joint fluid of a patient with arthritis or in the culture obtained in a medium including only 20% of joint fluid of a patient with arthritis.

EXAMPLE 12

Association of IL-17BR with Chondrogenic Differentiation Capability

UCB-MSC types having different chondrogenic differentiation capabilities were pellet cultured in a chondrogenic differentiation medium for 1 week to induce chondrogenic differentiation. The amount of mRNA of IL-17BR was measured by using a RT-PCR using a total RNA obtained by lysing the UCB-MSC as a template.

Figure 22:
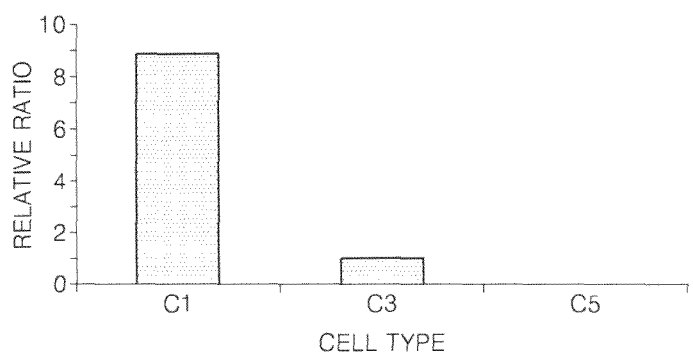
FIG. 22 is a graph showing results of analyzing the amount of mRNA of interleukin 17B receptor (IL-17BR) obtained by lysing an UCB-MSC differentiated into cartilage by a real time polymerase chain reaction (RT-PCR), according to an embodiment of the present invention.

FIG. 22 is a graph showing results of analyzing the amount of mRNA of IL-17BR obtained by lysing an UCB-MSC differentiated into cartilage by a RT-PCR, according to an embodiment of the present invention.

Referring to FIG. 22, an expression level of mRNA of IL-17BR varied according to the chondrogenic differentiation capability of the UCB-MSC. That is, the C2 and C3 UCB-MSC expressed mRNA of IL-17BR, and the degree of chondrogenic differentiation capability was 8.9 times higher in the C2 UCB-MSC than in the C3 UCB-MSC. On the other hand, the C5 UCB-MSC having a low chondrogenic differentiation capability did not express mRNA of IL-17BR.

EXAMPLE 13

The Effect of Joint Fluid of Patient with Arthritis on Expression of HB-EGF

An UCB-MSC was cultured in a medium to which a joint fluid of a patient with arthritis was added to a concentration of 10% (v/v) by using a method similar to that used in Example 1, for 6 hours, and the amount of mRNA of HB-EGF was measured by RT-PCR using a total RNA obtained from the UCB-MSC as a template. As a control, an UCB-MSC cultured under the same conditions described above, except that a medium did not include the joint fluid of a patient with arthritis, was used.

Figure 23:
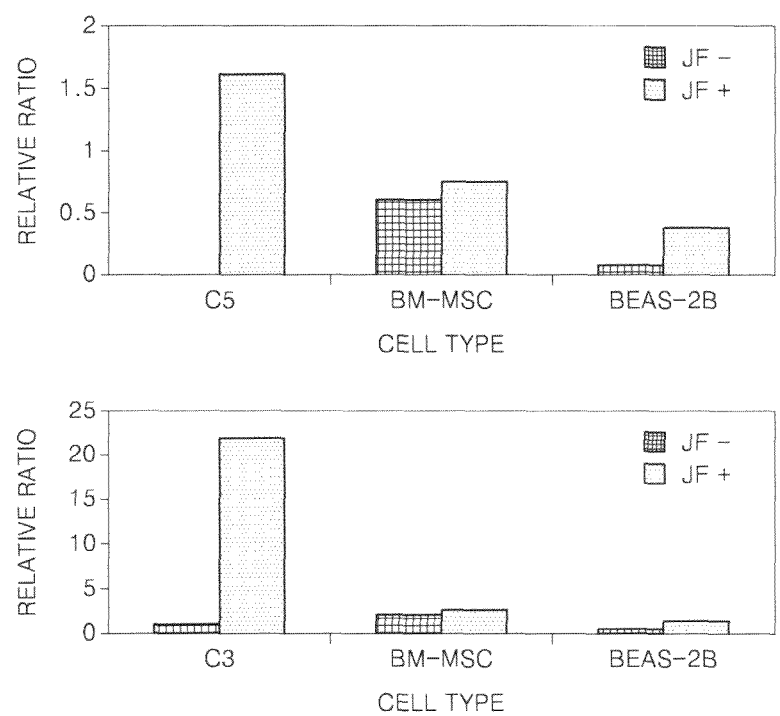
FIG. 23 illustrates graphs showing measurement results of mRNA of heparin-binding epidermal growth factor-like growth factor (HB-EGF) in an UCB-MSC cultured in the presence of a joint fluid of a patient with arthritis, according to an embodiment of the present invention.

FIG. 23 illustrates graphs showing measurement results of mRNA of HB-EGF in an UCB-MSC cultured in the presence of a joint fluid of a patient with arthritis, according to an embodiment of the present invention. In FIG. 23, C3 and C5 represent types of UCB-MSC, BM-MSC represents a bone marrow-derived mesenchymal stem cell, BEAS-2B represents a lung-derived bronchial epithelial cell, and JF represents a joint fluid. Referring to FIG. 23, the expression of HB-EGF in the UCB-MSC is significantly increased by the joint fluid of the patient with arthritis, while it is not significant in the BM-MSC and the BEAS-2B. The UCB-MSC expressed HB-EGF by the joint fluid of the patient with arthritis to an amount 2 times (C5 UCB-MSC) to 8.4 times (C3 UCB-MSC) larger than that of HB-EGF in the BM-MSC.

This indicates that the expression of HB-EGF is specifically induced in the UCB-MSC by the joint fluid of the patient with arthritis. This also indicates that the UCB-MSC may express a significantly larger amount of HB-EGF than that of HB-EGF in the BM-MSC.

In addition, an expression degree of HB-EGF by an UCB-MSC and in an UCB-MSC by the joint fluid of the patient with arthritis was measured. In this regard, C3 and C5 UCB-MSCs were used, and the joint fluids collected from 3 patients (JF1, JF5, and JF11) were used. The culturing conditions and measurement conditions of HB-EGF are the same as those described above in connection with FIG. 20. Table 1 shows results of analyzing an expression degree of HB-EGF by an UCB-MSC and in an UCB-MSC by joint fluids of patients with arthritis, by using RT-PCR.

TABLE 1

| HB-EGF | MSC | MSC + JF1 | MSC + JF5 | MSC + JF11 |
|---|---|---|---|---|
| C5 UCB-MSC | 1.00 | 9.80 | 26.60 | 9.20 |
| C3 UCB-MSC | 1.00 | 15.00 | 46.90 | 17.50 |

Referring to Table 1, when the UCB-MSC was cultured with the joint fluid of the patient with arthritis, it expressed HB-EGF to an amount 9.2 to 46.9 times larger than that of HB-EGF in the control.

EXAMPLE 14

Expression of HB-EGF by UCB-MSC Under Chondrocyte Death Conditions

An expression degree of HB-EGF by an UCB-MSC was analyzed under chondrocyte death conditions. First, a chondrocyte was separated from a joint of a 2-week-old rabbit. The separated chondrocyte was cultured in a medium containing a DMEM and 10% (v/v) FBS in a 6-well plate for 5 hours, and the chondrocyte being cultured was used in an experiment. The culturing of the UCB-MSC was performed in the presence of sodium nitroprusside (SNP) or the rabbit-derived chondrocyte for 24 hours. In this regard, 500 μM of SNP was added in the medium. SNP is a nitric oxide-producing compound, and is known to induce chondrocyte death. The addition of SNP is performed to simulate conditions arising in a patient with arthritis in vitro. In addition, the rabbit-derived chondrocyte and the UCB-MSC were respectively co-cultured on a lower portion and an upper portion of a transwell chamber (BD Falcon, San Jose, Calif., USA, Cell Culture inserts for 6-well plates, 0.4 μm, translucent PET membrane).

Whether HB-EGF is expressed or not was measured by performing immunoblotting such that the UCB-MSC was separated from the culture and lysed, and then an anti-HB-EGF antibody and an antibody specifically binding to an anti-HB-EGF antibody that were labeled with a fluorescence marker were used with respect to the same concentration of the lysate.

Figures 24, 25:
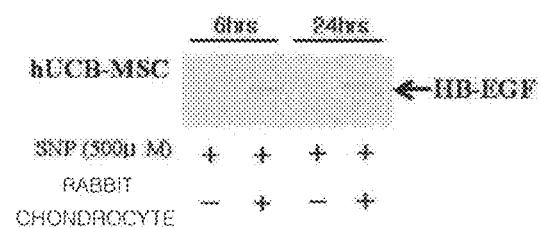
FIG. 24 is a diagram showing an expression amount of HB-EGF in an UCB-MSC cultured under chondrocyte death conditions, according to an embodiment of the present invention.
FIG. 25 illustrates images showing observation results of a rabbit-derived chondrocyte cultured in the presence of HB-EGF, according to an embodiment of the present invention.

FIG. 24 is a diagram showing an expression amount of HB-EGF in an UCB-MSC cultured under chondrocyte death conditions, according to an embodiment of the present invention. Referring to FIG. 24, the UCB-MSC did not express HB-EGF when it was cultured under chondrocyte apoptosis conditions, while the UCB-MSC expressed HB-EGF when it was co-cultured with the rabbit-derived chondrocyte.

In addition, the rabbit-derived chondrocyte was cultured in the presence of HB-EGF, and then it was confirmed whether the rabbit-derived chondrocyte was protected. FIG. 25 illustrates optical microscopic images showing observation results of a rabbit-derived chondrocyte cultured in the presence of HB-EGF, according to an embodiment of the present invention. Referring to FIG. 25, the rabbit-derived chondrocyte died depending on the concentration of SNP in the control (upper portion), while the apoptosis of the rabbit-derived chondrocyte cultured in a medium containing 50 ng/ml of HB-EGF was inhibited depending on the concentration of SNP. This indicates that the apoptosis of the rabbit-derived chondrocyte caused by SNP is inhibited by HB-EGF.

The sequence list enclosed in the present specification is for reference purposes.

A composition including TSP-2, according to an embodiment of the present invention, may stimulate differentiation of a cell, for example, an MSC, into a chondrocyte.

According to one or more embodiments of the present invention, there is provided a method of identifying a capability of a cell, for example, an MSC, to differentiate into a chondrocyte, by using TSP-1, TSP-2, or IL-17BR, whereby a chondrogenic differentiation capability of the MSC may be efficiently identified.

According to one or more embodiments of the present invention, there is provided a method of differentiating a cell, for example, an MSC, into a chondrocyte, by using TSP-1, TSP-2, or IL-17BR, whereby the cell, for example, the MSC, may be efficiently differentiated into a chondrocyte.

According to an embodiment of the present invention, there is provided a method of differentiating a cell, for example, an MSC, into a lesion tissue cell, whereby the cell, for example, the MSC, may be efficiently differentiated into a lesion tissue cell.

According to an embodiment of the present invention, there is provided a method screening a material regulating cell activity, for example, activity of an MSC, whereby a material regulating the cell activity, for example, activity of the MSC, may be efficiently screened.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method of selecting a stem cell capable of differentiating into a chondrocyte or inducing chondrocyte differentiation, the method comprising:
   culturing a stem cell in a monolayer or pellet in a maintenance medium;
   measuring a concentration of TSP-2; and
   selecting and isolating a stem cell having a high chondrogenic differentiation capability from the culture medium if
   a) the concentration of TSP-2 in cell culture is larger than 72 pg/ml/$1.0 \times 10^5$ cells when the stem cell is monolayer cultured for 1 day, or
   b) the concentration of TSP-2 in cell culture is larger than 550 pg/ml/$1.0 \times 10^5$ cells when the stem cell is pellet cultured for 7 days,
   wherein the selected stem cell is capable of differentiating into a chondrocyte or inducing chondrocyte differentiation.

2. The method of claim 1, wherein the stem cell is an umbilical cord blood mesenchymal stem cell (UCB-MSC).

3. The method of claim 1, wherein the stem cell may be selected from the group consisting of an induced pluripotent stem cell (iPS cell), an embryonic stem cell, and an adult stem cell.

4. The method of claim 1, wherein the stem cell may be selected from the group consisting of a mesenchymal stem cell (MSC), an adipose-derived stem cell, an endothelial stem cell, and a hematopoietic stem cell.

5. The method of claim 1, wherein said method further comprises differentiating said stem cells in vitro or in vivo.

* * * * *